(12) United States Patent
Loccufier

(10) Patent No.: US 8,957,224 B2
(45) Date of Patent: *Feb. 17, 2015

(54) PHOTOINITIATORS FOR UV-LED CURABLE COMPOSITIONS AND INKS

(75) Inventor: Johan Loccufier, Zwijnaarde (BE)

(73) Assignee: Agfa Graphics NV, Mortsel (BE)

( * ) Notice: Subject to any disclaimer, the term of this patent is extended or adjusted under 35 U.S.C. 154(b) by 215 days.

This patent is subject to a terminal disclaimer.

(21) Appl. No.: 13/511,375

(22) PCT Filed: Dec. 6, 2010

(86) PCT No.: PCT/EP2010/068940
§ 371 (c)(1),
(2), (4) Date: May 23, 2012

(87) PCT Pub. No.: WO2011/069947
PCT Pub. Date: Jun. 16, 2011

(65) Prior Publication Data
US 2012/0309861 A1  Dec. 6, 2012

Related U.S. Application Data

(60) Provisional application No. 61/267,468, filed on Dec. 8, 2009.

(30) Foreign Application Priority Data

Dec. 7, 2009  (EP) .................................... 09178164

(51) Int. Cl.
| | | |
|---|---|---|
| *C07D 209/82* | (2006.01) | |
| *C07D 209/86* | (2006.01) | |
| *C08J 3/28* | (2006.01) | |
| *C08F 2/46* | (2006.01) | |
| *C08F 2/50* | (2006.01) | |
| *G03F 7/031* | (2006.01) | |

(52) U.S. Cl.
CPC ................ *C07D 209/86* (2013.01); *C08F 2/50* (2013.01); *G03F 7/031* (2013.01)
USPC ............... 548/444; 548/440; 548/441; 522/6; 522/14; 522/28; 522/26; 522/35; 522/50; 522/49; 522/63

(58) Field of Classification Search
USPC ............ 548/440, 441, 444; 522/14, 6, 26, 28, 522/35, 50, 49, 63
See application file for complete search history.

(56) References Cited

U.S. PATENT DOCUMENTS

| 4,987,159 | A | 1/1991 | Li Bassi et al. |
| 8,569,393 | B2 * | 10/2013 | Loccufier ........................ 522/14 |
| 2003/0199601 | A1 | 10/2003 | Chang et al. |
| 2005/0113483 | A1 | 5/2005 | Takabayashi |
| 2006/0014848 | A1 | 1/2006 | Loccufier et al. |

FOREIGN PATENT DOCUMENTS

| DE | 199 28 742 A1 | 12/1999 |
| EP | 0 006 173 A1 | 1/1980 |
| EP | 0 284 561 A2 | 9/1988 |
| EP | 1 395 615 A1 | 3/2004 |
| EP | 1 567 518 A2 | 8/2005 |
| EP | 2 053 101 A1 | 4/2009 |
| JP | 63-168403 A | 7/1988 |
| JP | 2000-239648 A | 9/2000 |
| JP | 2001-109142 A | 4/2001 |
| JP | 2005-113043 A | 4/2005 |
| JP | 2005-187678 A | 7/2005 |
| JP | 2005-343847 A | 12/2005 |
| JP | 2006-162784 A | 6/2006 |
| JP | 2007-112930 A | 5/2007 |
| JP | 2007-219362 A | 8/2007 |
| JP | 2007-254701 A | 10/2007 |
| JP | 2009221334 A * | 10/2009 |
| SU | 696 017 A1 | 11/1979 |
| WO | 00/00869 A1 | 1/2000 |
| WO | 00/10972 A1 | 3/2000 |
| WO | 00/52530 A1 | 9/2000 |
| WO | 01/19939 A1 | 3/2001 |
| WO | 02/100903 A1 | 12/2002 |
| WO | 2004/050653 A2 | 6/2004 |
| WO | 2006/018405 A1 | 2/2006 |
| WO | 2006/059458 A1 | 6/2006 |
| WO | 2007/062963 A1 | 6/2007 |
| WO | 2007/071497 A1 | 6/2007 |
| WO | 2008/075564 A1 | 6/2008 |
| WO | 2008/138724 A1 | 11/2008 |
| WO | 2008/138732 A1 | 11/2008 |
| WO | 2008/138733 A1 | 11/2008 |

OTHER PUBLICATIONS

Official Communication issued in International Patent Application No. PCT/EP2010/068940, mailed on May 23, 2011.
Loccufier, "UV-LED curable compositions and inks," U.S. Appl. No. 13/511,374, filed May 23, 2012.
Chen et al., "Photosensitization of Carbazole Derivatives in Cationic Polymerization with a Novel Sensitivity to Near-UV Light," Journal of Polymer Science: Part A: Polymer Chemistry, vol. 38, 2000, pp. 90-100.
Dietliker et al., "Advancements in Photoinitiators—Opening Up New Applications for Radiation Curing," Progress in Organic Coatings 58, 2007, pp. 146-157.
Laurich et al., "Photochemistry of 1- and 2-Naphthylglyoxylic Acid," Journal of Photochemistry and Photobiology A: Chemistry, vol. 112, 1998, pp. 29-38.
Pastors et al., "Synthesis of Some Carbazoleacetic Acids," Khimicheskaya Tekhnologiya Biologicheski Aktivnykh Soedinenii, vol. 2, 1983, pp. 78-82.

* cited by examiner

*Primary Examiner* — Sanza McClendon
(74) *Attorney, Agent, or Firm* — Keating & Bennett, LLP

(57) ABSTRACT

A specific type of carbazole photoinitiator is capable of providing radiation curable compositions that are curable by UV LEDs and do not exhibit an unstable yellowing behavior in an image upon storage like ITX.

20 Claims, No Drawings

PHOTOINITIATORS FOR UV-LED CURABLE COMPOSITIONS AND INKS

CROSS-REFERENCE TO RELATED APPLICATIONS

This application is a 371 National Stage Application of PCT/EP2010/068940, filed Dec. 6, 2010. This application claims the benefit of U.S. Provisional Application No. 61/267,468, filed Dec. 8, 2009, which is incorporated by reference herein in its entirety. In addition, this application claims the benefit of European Application No. 09178164.1, filed Dec. 7, 2009, which is also incorporated by reference herein in its entirety.

BACKGROUND OF THE INVENTION

1. Field of the Invention

The present invention relates to a new class of photoinitiators, especially suited for UV LED curable compositions.

2. Description of the Related Art

Photoinitiators are frequently used in polymerizable compositions, such as UV-curable inks, to initiate the polymerization of monomers when exposed to UV radiation. Bathochromic photoinitiators, absorbing in the region between 365 nm and 395 nm, are required to make full use of the recent development of UV-LEDs with increasing power. Thioxanthones and acyl phosphine oxides are photoinitiators absorbing in this spectral region.

Thioxanthones are prone to yellowing upon exposure, thereby forming degradation products with a limited stability. As a result, the original yellowing shifts upon storage. Especially in imaging, e.g. inkjet printing, this unstable yellowing behaviour makes control of the image tone in the final image difficult. On top of that, certain applications, predominantly packaging applications, prefer thioxanthone free radiation curable compositions.

Acyl phosphine oxides, on the other hand, result in medium volatile aldehyde type of degradation products, resulting in a background smell of the printed image, which is unacceptable in packaging applications.

Therefore, there is an increasing demand for the development of new photoinitiators, absorbing in the region between 365 nm and 395 nm, having a stable yellowing behaviour without generating medium volatile degradation products. Recent evolutions in bathochromic photoinitiators are based on carbazole derivatives.

Much effort in carbazole based initiators has been directed towards the development N-acyl oxime derivatives of bis ketocarbazoles as photoinitiators for black resists as recently reviewed by Dietliker et al. (Progress in Organic Coatings 58, 146-157 (2007) and disclosed in WO 2008/138733 (CIBA), WO 2008/138732 (CIBA), WO 2008/138724 (CIBA), WO 2007/071497 (CIBA), WO 2007/062963 (CIBA), WO 2006/018405 (CIBA), WO 2004/050653 (CIBA), WO 02/100903 (CIBA), WO 2008/075564 (MITSUBISHI CHEMICAL) and WO 2006/059458 (ASAHI DENKA).

Carbazole based Norrish type I initiators have been disclosed in JP 2007-254701 (TOYO INK), US 2003199601 (SAMSUNG ELECTRONICS), JP 63-168403 (FUJI PHOTO FILM) and EP 284561 A (CIBA)).

Bis-keto-carbazoles have been disclosed in photochemical applications as sensitizers for acyl oxime and oxime based photoinitiators in negative resist application (JP 2007-219362 (TOYO INK)) and radiation curable applications JP 2007-112930 (TOYO INK) and JP 2005-187678 (TOYO INK)). They have further been disclosed as sensitizing agents for cationic radiation curable formulations in US 2005113483 (KONICA), JP 2005-343847 (TOYO INK), JP 2000239648 (JSR) and Yamamura et al., Journal of Photopolymer Science and Technology, 13(1), 117-118 (2000)) and JP 2001-109142 (JSR)).

The carbazole initiators, disclosed in the prior art often require multistep synthesis and are often still to hypsochromic to be cured by LED curing. Therefore, there is still a need for easy accessible photoinitiators exhibiting high curing speed upon LED exposure.

SUMMARY OF THE INVENTION

In order to overcome the problems described above, it has been surprisingly found that a specific carbazole based photoinitiator provided radiation curable compositions with high curing speed upon exposure to UV radiation in the range between 365 nm and 395 nm.

According to preferred embodiments of the present invention, a photoinitiator having a much more stable yellowing behaviour and without generating medium volatile degradation products can be achieved, as defined below.

Other features, elements, steps, characteristics and advantages of the present invention will become more apparent from the following detailed description of preferred embodiments of the present invention hereinafter.

DETAILED DESCRIPTION OF THE PREFERRED EMBODIMENTS

The term "C.I." is used in disclosing the present application as an abbreviation for Colour Index.

The term "alkyl" means all variants possible for each number of carbon atoms in the alkyl group i.e. for three carbon atoms: n-propyl and isopropyl; for four carbon atoms: n-butyl, isobutyl and tertiary-butyl; for five carbon atoms: n-pentyl, 1,1-dimethyl-propyl, 2,2-dimethylpropyl and 2-methyl-butyl etc.

The term "substituted" in, for example substituted alkyl, means that the substituent contains at least one atom different from carbon or hydrogen. The substituent may be a single atom (e.g. a halogen) or a group of atoms containing at least one atom different from carbon or hydrogen (e.g. an acrylate group).

Photoinitiators

A photoinitiator according to a preferred embodiment of present invention has as chemical structure the Formula (I):

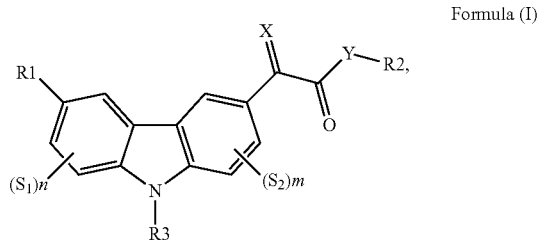

Formula (I)

wherein,

R1 selected from the group consisting of a group according to S1, —CN, —COR4 and a functional group according to Formula (II):

Formula (II)

R2 and R5 are independently selected from the group consisting of hydrogen a substituted or unsubstituted alkyl group, a substituted or unsubstituted alkenyl group, a substituted or unsubstituted alkynyl group, a substituted or unsubstituted aralkyl group, a substituted or unsubstituted alkaryl group and a substituted or unsubstituted aryl or heteroaryl group;

S1 and S2 are independently selected from the group consisting of hydrogen, a substituted or unsubstituted alkyl group, a substituted or unsubstituted alkenyl group, a substituted or unsubstituted alkynyl group, a substituted or unsubstituted aralkyl group, a substituted or unsubstituted alkaryl group, a substituted or unsubstituted aryl, a substituted or unsubstituted heteroaryl group, a halogen, OH, an alkoxy group, a thiol group, a thioalkoxy group, an ester group, an amide group, an amine group and a carboxylic acid group;

R3 is selected from the group consisting of hydrogen, a substituted or unsubstituted alkyl group, a substituted or unsubstituted alkenyl group, a substituted or unsubstituted alkynyl group, a substituted or unsubstituted aralkyl group, a substituted or unsubstituted alkaryl group and a substituted or unsubstituted aryl or heteroaryl group;

R4 is selected from the group consisting of a hydrogen a substituted or unsubstituted alkyl group, a substituted or unsubstituted alkenyl group, a substituted or unsubstituted alkynynl group, a substituted or unsubstituted aralkyl group, a substituted or unsubstituted alkaryl group, a substituted or unsubstituted aryl or heteroaryl group and W—R6;

Q and X independently represent O or N—R7;

W, V and Y independently represent O or N—R8;

R6 and R8 independently are selected from the group consisting of hydrogen a substituted or unsubstituted alkyl group, a substituted or unsubstituted alkenyl group, a substituted or unsubstituted alkynyl group, a substituted or unsubstituted aralkyl group, a substituted or unsubstituted alkaryl group and a substituted or unsubstituted aryl or heteroaryl group;

R7 is selected from the group consisting a hydrogen a substituted or unsubstituted alkyl group, a substituted or unsubstituted alkenyl group, a substituted or unsubstituted alkynyl group, a substituted or unsubstituted aralkyl group, a substituted or unsubstituted alkaryl group, a substituted or unsubstituted aryl or heteroaryl group and O—R9;

R9 is selected from the group consisting of hydrogen a substituted or unsubstituted alkyl group, a substituted or unsubstituted alkenyl group, a substituted or unsubstituted alkynyl group, a substituted or unsubstituted aralkyl group, a substituted or unsubstituted alkaryl group, a substituted or unsubstituted aryl or heteroaryl group and an acyl group;

n and m independently represent an integer from 1 to 3;

with the proviso that at least one of R1 to R3 comprises a branched, substituted or unsusbtituted alkyl, alkenyl, alkynyl, aralkyl or alkaryl group.

In a preferred embodiment, R1 is selected from the group consisting of hydrogen, —COR4 and a functional group according to Formula (II). In a further preferred embodiment, Q an X represent O.

In an even further preferred embodiment, $S_1$ and $S_2$ represent hydrogen. In the most preferred embodiment R3 represents a branched alkyl group.

In a preferred embodiment, the photoinitiator, according to the present invention is a diffusion hindered photoinitiator selected from the group consisting of a polymerisable photoinitiator, a multifunctional photoinitiator and a polymeric or an oligomeric photoinitiator. Preferred polymeric photoinitiators, according to the present invention are selected from the group consisting of star polymers, dendritic polymers and hyperbranched polymers, polyesters and polyethers being particularly preferred.

In a particularly preferred embodiment, the photoinitiator according to the present invention is a photoinitiator according to Formula (III):

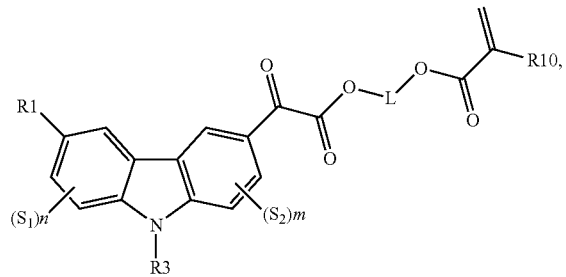

Formula (III)

wherein,

R1, R3, $S_1$, $S_2$, n and m are defined as for Formula (I);

L is a divalent linking group comprising 1 to 15 carbon atoms;

R10 represents a hydrogen or a C1 to C4 alkyl group, a hydrogen and a methyl group being particularly preferred and a hydrogen being most preferred.

Suitable examples of photoinitiators according to Formula (I) are given by Table 1, without being limited thereto.

TABLE 1

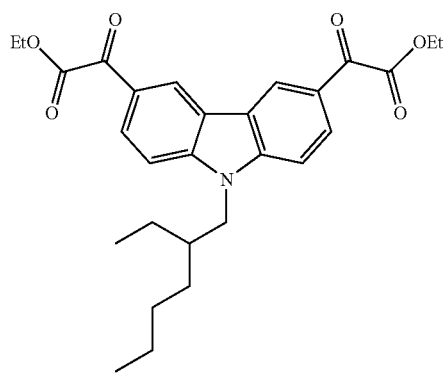 [SMILES: CCCCC(CC)Cn1c2ccc(C(=O)C(=O)OCC)cc2c2cc(C(=O)C(=O)OCC)ccc21]

INI-1

TABLE 1-continued
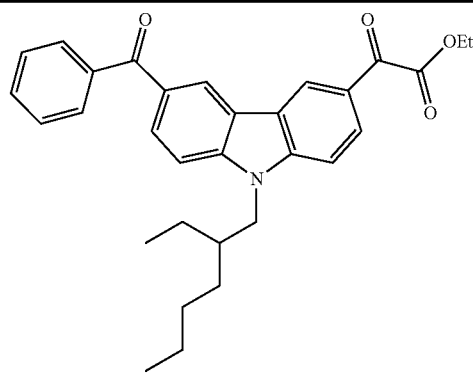
INI-2
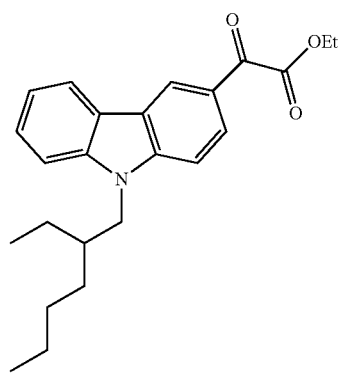 [SMILES: CCCCC(CC)Cn1c2ccccc2c2cc(C(=O)C(=O)OCC)ccc21]
INI-3
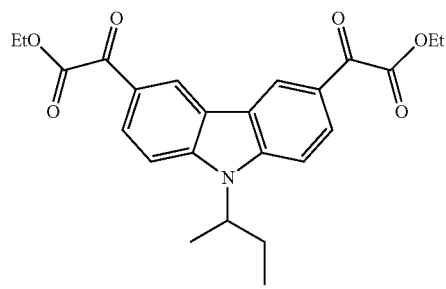 [SMILES: CCOC(=O)C(=O)c1ccc2c(c1)c1cc(C(=O)C(=O)OCC)ccc1n2C(C)CC]
INI-4
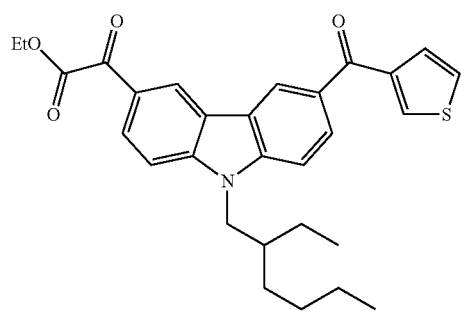 [SMILES: CCCCC(CC)Cn1c2ccc(C(=O)C(=O)OCC)cc2c2cc(C(=O)c3ccsc3)ccc21]
INI-5
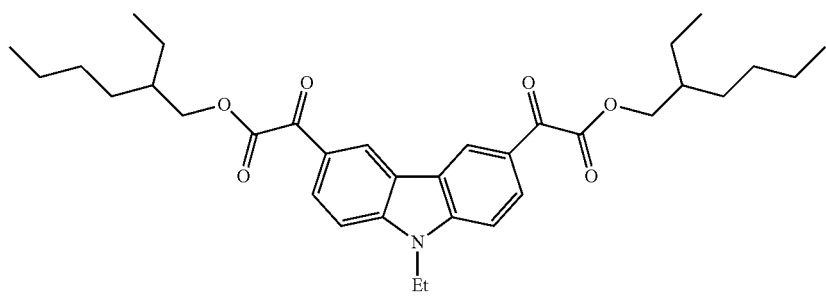 [SMILES: CCCCC(CC)COC(=O)C(=O)c1ccc2c(c1)c1cc(C(=O)C(=O)OCC(CC)CCCC)ccc1n2CC]
INI-6

TABLE 1-continued
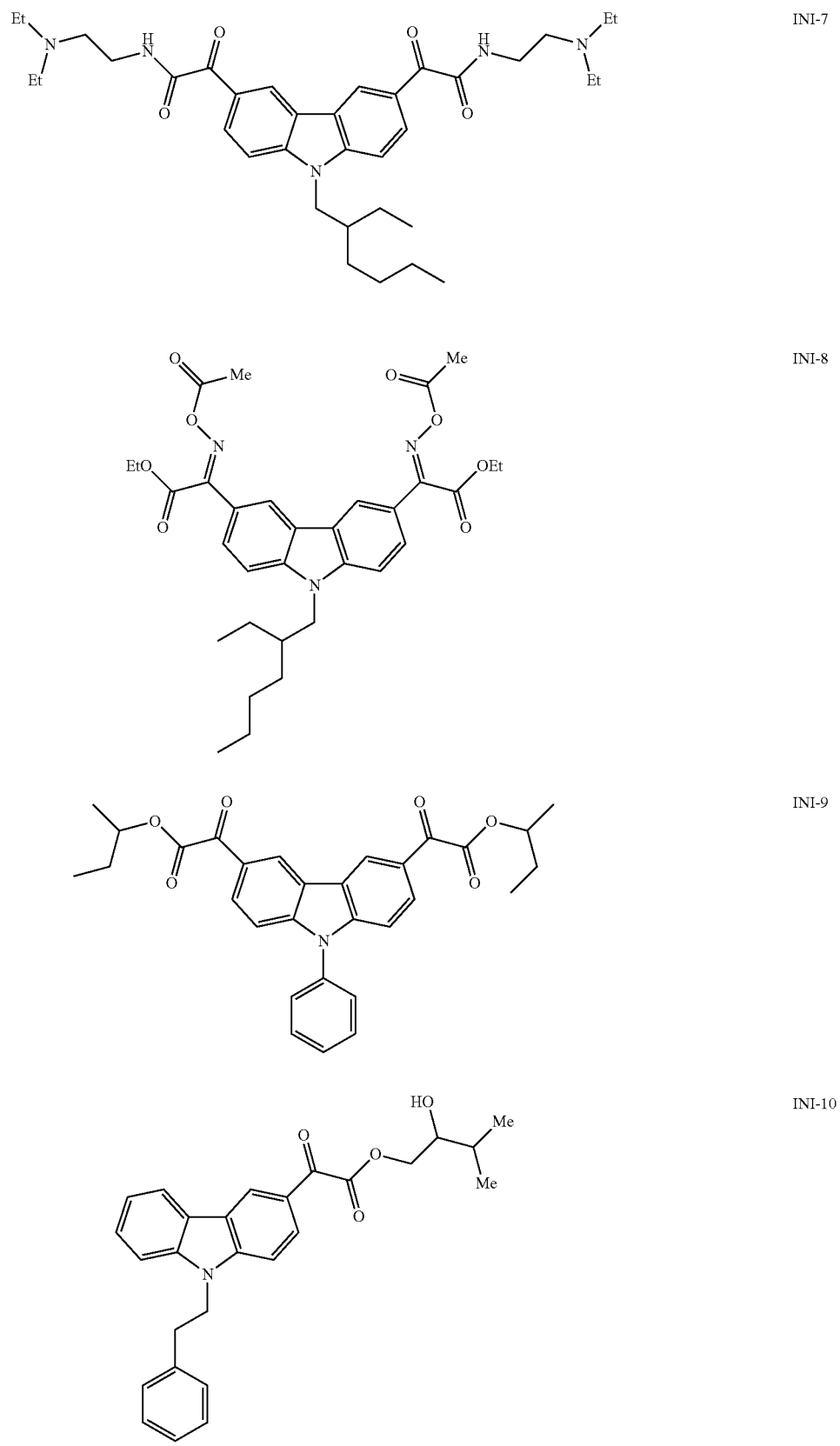
INI-7
INI-8
INI-9
INI-10

TABLE 1-continued
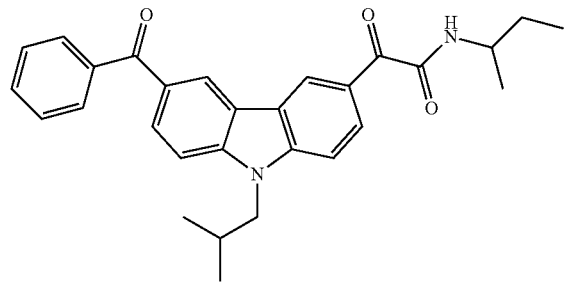 [SMILES: CCC(C)NC(=O)C(=O)c1ccc2c(c1)c1cc(C(=O)c3ccccc3)ccc1n2CC(C)C]
INI-11
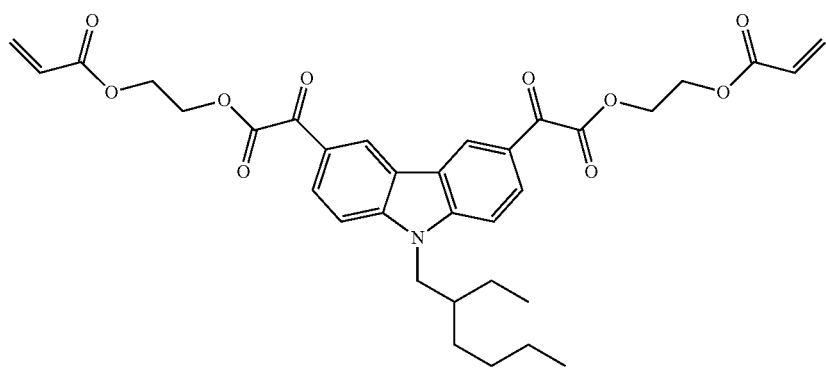 [SMILES: C=CC(=O)OCCOC(=O)C(=O)c1ccc2c(c1)c1cc(C(=O)C(=O)OCCOC(=O)C=C)ccc1n2CC(CC)CCCC]
INI-12
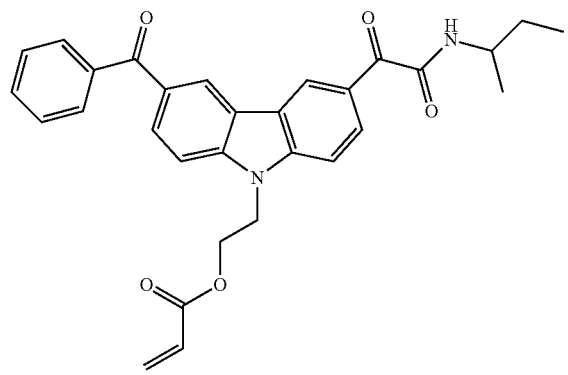 [SMILES: C=CC(=O)OCCn1c2ccc(C(=O)C(=O)NC(C)CC)cc2c2cc(C(=O)c3ccccc3)ccc21]
INI-13
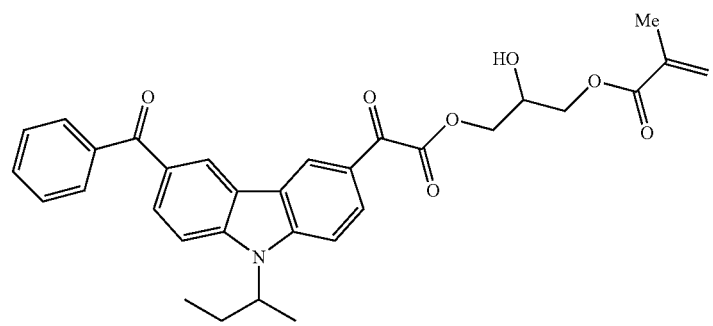 [SMILES: C=C(C)C(=O)OCC(O)COC(=O)C(=O)c1ccc2c(c1)c1cc(C(=O)c3ccccc3)ccc1n2C(C)CC]
INI-14

TABLE 1-continued
INI-15
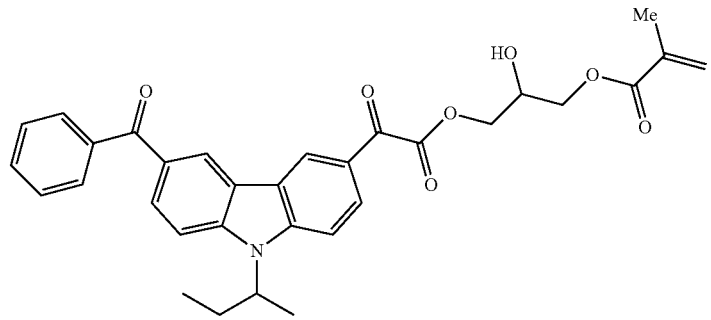 [SMILES: C=C(C)C(=O)OCC(O)COC(=O)C(=O)c1ccc2c(c1)c1cc(C(=O)c3ccccc3)ccc1n2C(C)CC]
INI-16
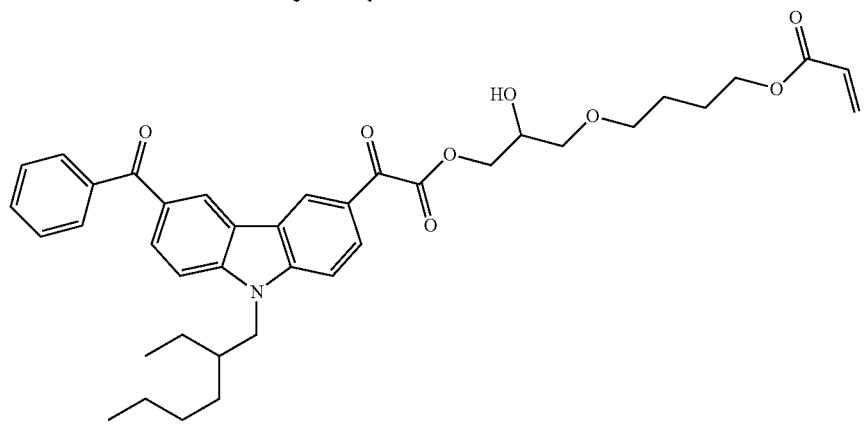
INI-17
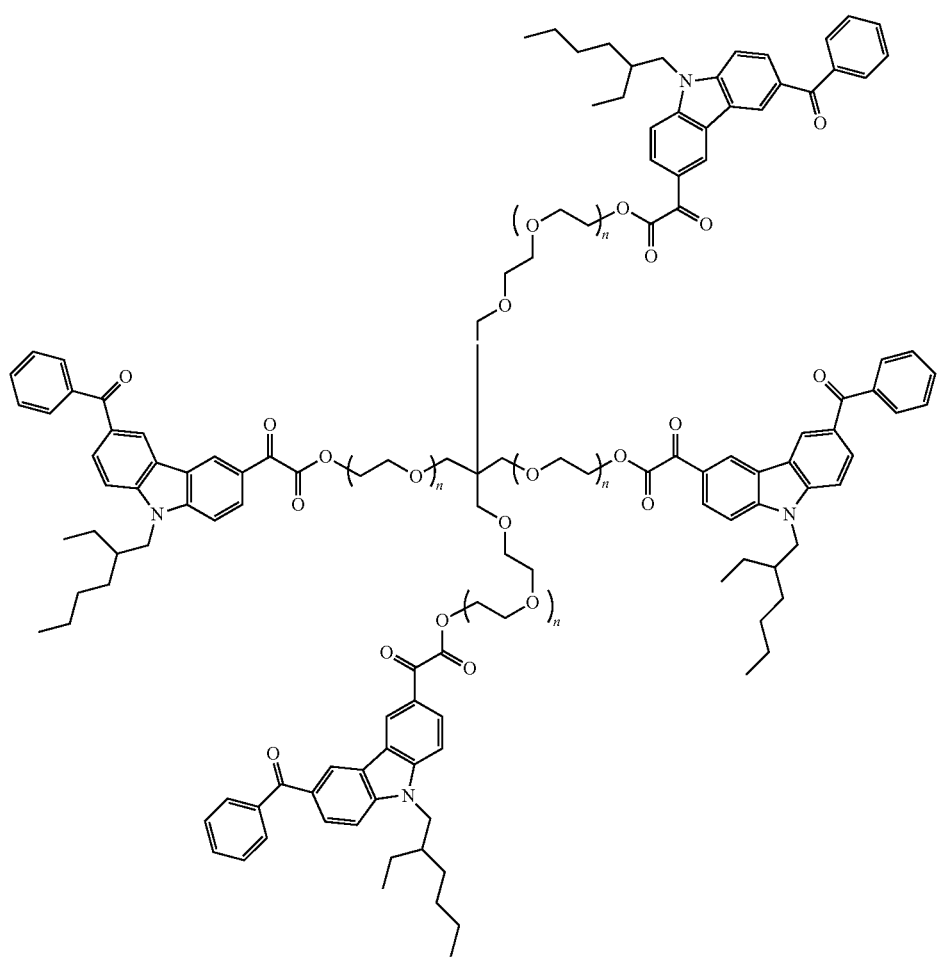

TABLE 1-continued

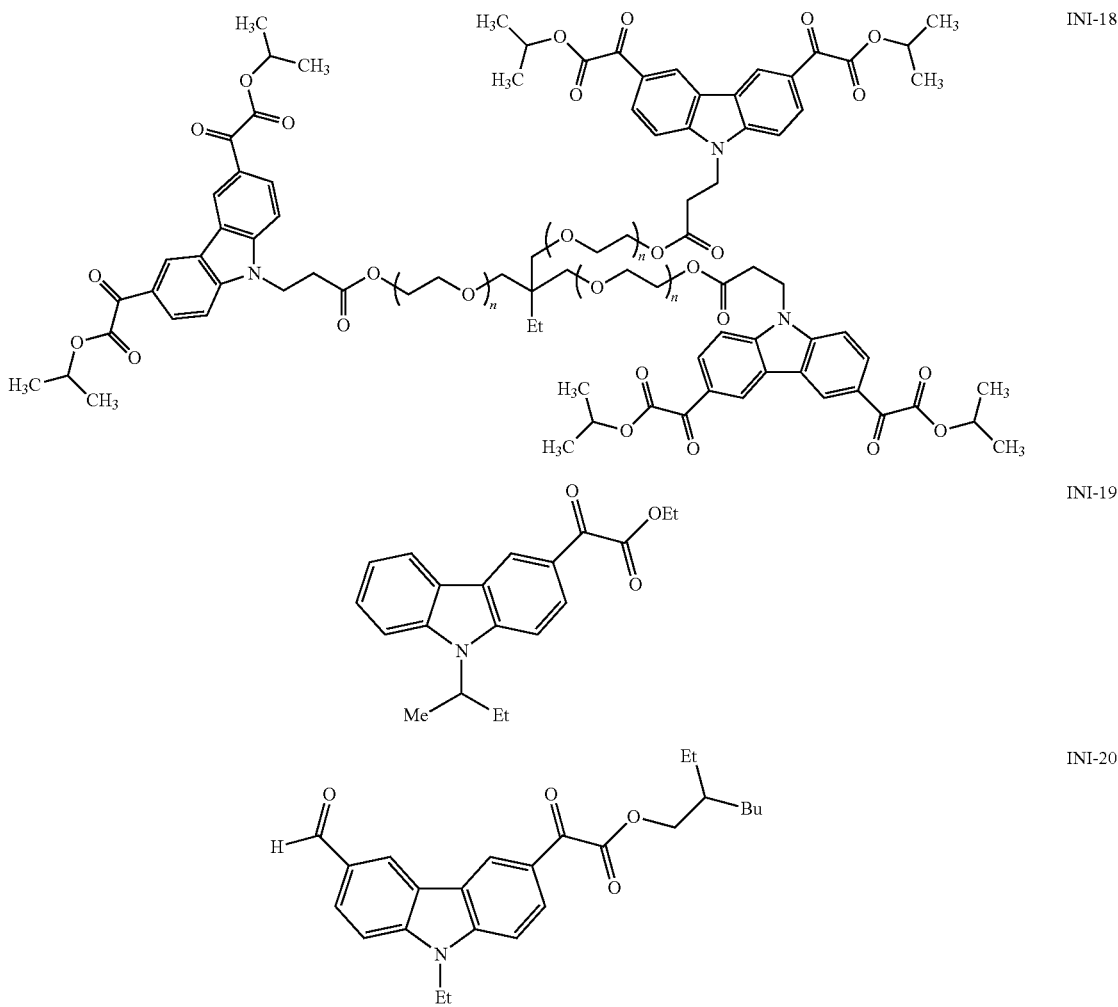

For safety reasons, in particular for food packaging applications, the photoinitiator is preferably a so-called diffusion hindered photoinitiator. A diffusion hindered photoinitiator is a photoinitiator which exhibits a much lower mobility in a cured layer of the curable liquid or ink than a monofunctional photoinitiator, such as benzophenone. Several methods can be used to lower the mobility of the photoinitiator. One way is to increase the molecular weight of the photoinitiator so that the diffusion speed is reduced, e.g. polymeric photoinitiators. Another way is to increase its reactivity so that it is built into the polymerizing network, e.g. multifunctional photoinitiators and polymerizable photoinitiators. The diffusion hindered photoinitiator is preferably selected from the group consisting of non-polymeric multifunctional photoinitiators, polymeric photoinitiators and polymerizable photoinitiators. Non-polymeric multifunctional photoinitiators are considered to have a molecular weight between 300 and 900 Dalton. Non-polymerizable monofunctional photoinitiators with a molecular weight in that range are not diffusion hindered photoinitiators. Most preferably the diffusion hindered photoinitiator is a polymerizable initiator.

Suitable polymerizable photoinitiators according to Formula (I) are given in Table 1 by the photoinitiators INI-12 to INI-16.

A preferred amount of photoinitiator is 0.1-50 wt %, more preferably 0.1-20 wt %, and most preferably 0.3-15 wt % of the total weight of the curable pigment dispersion or ink.

Radiation Curable Compositions

The photoinitiators according to a preferred embodiment of the present invention can be advantageously used in radiation curable compositions to prevent unstable yellowing behaviour in an image upon storage, e.g. an inkjet image.

In a preferred embodiment, the radiation curable composition is a radiation curable inkjet ink, especially an inkjet ink curable by UV LEDs emitting at in the spectral region of 365 nm to 395 nm. Due to their compactness, UV LEDs can be built into inkjet printers more easily than other UV light sources such as doped mercury lamps.

In a preferred embodiment, the radiation curable inkjet ink is part of an inkjet ink set, preferably an inkjet ink set including two or more inkjet inks in accordance with the invention. The radiation curable inkjet ink form preferably part of a CMY(K) inkjet ink set. The CMY(K) inkjet ink set may also be extended with extra inks such as red, green, blue, violet and/or orange to further enlarge the colour gamut of the image. The CMY(K) ink set may also be extended by the combination of full density and light density inks of both colour inks and/or black inks to improve the image quality by lowered graininess.

The inkjet ink can be advantageously used in an inkjet printing method comprising the steps:
a) providing a radiation curable inkjet ink according to a preferred embodiment of the present invention; and
b) jetting the inkjet ink onto an ink-receiver.

The radiation curable composition according to a preferred embodiment of the present invention may further also contain at least one surfactant to control the homogenous spreading of the pigment dispersion on a substrate. For an inkjet ink, the surfactant is important to control the dot size of the ink droplet on a substrate.

There is no limitation on the viscosity of the radiation curable composition, but the viscosity of a radiation curable inkjet ink is preferably lower than 30 mPa·s, more preferably lower than 15 mPa·s, and most preferably between 2 and 10 mPa·s at a shear rate of 100 s$^{-1}$ and a jetting temperature between 10 and 70° C.

The radiation curable composition according to the present invention is preferably prepared according to a method comprising the steps of:
a) providing a composition containing monomers;
b) adding to said composition at least one co-initiator selected from the group consisting of an aliphatic tertiary amine and a dialkyl aniline derivative; and at least one photoinitiator according to Formula (I).

Co-Initiators

In order to increase the photosensitivity further, the radiation curable composition contains a co-initiator. Suitable examples of co-initiators can be categorized in 3 groups:
(1) tertiary aliphatic amines such as methyldiethanolamine, dimethylethanolamine, triethanolamine, triethylamine and N-methylmorpholine;
(2) aromatic amines such as amylparadimethylaminobenzoate, 2-n-butoxyethyl-4-(dimethylamino) benzoate, 2-(dimethylamino)ethylbenzoate, ethyl-4-(dimethylamino)benzoate, and 2-ethylhexyl-4-(dimethylamino)benzoate; and
(3) (meth)acrylated amines such as dialkylamino alkyl(meth) acrylates (e.g., diethylaminoethylacrylate) or N-morpholinoalkyl-(meth)acrylates (e.g., N-morpholinoethyl-acrylate).

The preferred co-initiators are aminobenzoates.

The one or more co-initiators included into the radiation curable composition according to a preferred embodiment of the present invention are preferably diffusion hindered for safety reasons, in particular for food packaging applications.

A diffusion hindered co-initiator is preferably selected from the group consisting of non-polymeric multifunctional co-initiators, oligomeric or polymeric co-initiators and polymerizable co-initiators. More preferably the diffusion hindered co-initiator is selected from the group consisting of polymeric co-initiators and polymerizable co-initiators. Most preferably the diffusion hindered co-initiator is a polymerizable co-initiator having at least one (meth)acrylate group, more preferably having at least one acrylate group.

Preferred diffusion hindered co-initiators are the polymerizable co-initiators disclosed in EP 2053101 A (AGFA GRAPHICS) in paragraphs [0088] and [0097].

Preferred diffusion hindered co-initiators include a polymeric co-initiator having a dendritic polymeric architecture, more preferably a hyperbranched polymeric architecture. Preferred hyperbranched polymeric co-initiators are those disclosed in US 2006014848 (AGFA) incorporated herein as a specific reference.

The curable pigment dispersion or ink preferably comprises the diffusion hindered co-initiator in an amount of 0.1 to 50 wt %, more preferably in an amount of 0.5 to 25 wt %, most preferably in an amount of 1 to 10 wt % of the total weight of the ink.

Monomers and Oligomers

The monomers and oligomers used in radiation curable compositions and inks, especially for food packaging applications, are preferably purified compounds having no or almost no impurities, more particularly no toxic or carcinogenic impurities. The impurities are usually derivative compounds obtained during synthesis of the polymerizable compound. Sometimes, however, some compounds may be added deliberately to pure polymerizable compounds in harmless amounts, for example, polymerization inhibitors or stabilizers.

Any monomer or oligomer capable of free radical polymerization may be used as polymerizable compound. A combination of monomers, oligomers and/or prepolymers may also be used. The monomers, oligomers and/or prepolymers may possess different degrees of functionality, and a mixture including combinations of mono-, di-, tri- and higher functionality monomers, oligomers and/or prepolymers may be used. The viscosity of the radiation curable compositions and inks can be adjusted by varying the ratio between the monomers and oligomers.

Particularly preferred monomers and oligomers are those listed in [0106] to [0115] in EP 1911814 A (AGFA GRAPHICS) incorporated herein as a specific reference.

A preferred class of monomers and oligomers are vinyl ether acrylates such as those described in U.S. Pat. No. 6,310, 115 (AGFA), incorporated herein by reference. Particularly preferred compounds are 2-(2-vinyloxyethoxy)ethyl(meth) acrylate, most preferably the compound is 2-(2-vinyloxyethoxy)ethyl acrylate.

Colorants

Colorants used in the radiation curable compositions and inks may be dyes, pigments or a combination thereof. Organic and/or inorganic pigments may be used. The colorant is preferably a pigment or a polymeric dye, most preferably a pigment.

The pigments may be black, white, cyan, magenta, yellow, red, orange, violet, blue, green, brown, mixtures thereof, and the like. This colour pigment may be chosen from those disclosed by HERBST, Willy, et al. Industrial Organic Pigments, Production, Properties, Applications. 3rd edition. Wiley—VCH, 2004. ISBN 3527305769.

Suitable pigments are disclosed in paragraphs [0128] to [0138] of WO 2008/074548 (AGFA GRAPHICS).

Suitable pigments include mixed crystals of the above particular preferred pigments. Mixed crystals are also referred to as solid solutions. For example, under certain conditions different quinacridones mix with each other to form solid solutions, which are quite different from both physical mixtures of the compounds and from the compounds themselves. In a solid solution, the molecules of the components enter into the same crystal lattice, usually, but not always, that of one of the components. The x-ray diffraction pattern of the resulting crystalline solid is characteristic of that solid and can be clearly differentiated from the pattern of a physical mixture of the same components in the same proportion. In such physical mixtures, the x-ray pattern of each of the components can be distinguished, and the disappearance of many of these lines is one of the criteria of the formation of solid solutions. A commercially available example is Cinquasia Magenta RT-355-D from Ciba Specialty Chemicals.

Also mixtures of pigments may be used in the UV curable inks. For some inkjet applications, a neutral black inkjet ink is preferred and can be obtained, for example, by mixing a black pigment and a cyan pigment into the ink. The inkjet application may also require one or more spot colours, for example for packaging inkjet printing or textile inkjet printing. Silver and gold are often desired colours for inkjet poster printing and point-of-sales displays.

Non-organic pigments may be used in the radiation curable compositions and inks. Particular preferred pigments are C.I. Pigment Metal 1, 2 and 3. Illustrative examples of the inorganic pigments include red iron oxide (III), cadmium red, ultramarine blue, prussian blue, chromium oxide green, cobalt green, amber, titanium black and synthetic iron black.

Pigment particles in inkjet inks should be sufficiently small to permit free flow of the ink through the inkjet-printing device, especially at the ejecting nozzles. It is also desirable to use small particles for maximum colour strength and to slow down sedimentation.

The numeric average pigment particle size is preferably between 0.050 and 1 μm, more preferably between 0.070 and 0.300 μm and particularly preferably between 0.080 and 0.200 μm. Most preferably, the numeric average pigment particle size is no larger than 0.150 μm. An average particle size smaller than 0.050 μm is less desirable for decreased light-fastness, but mainly also because very small pigment particles or individual pigment molecules thereof may still be extracted in food packaging applications. The average particle size of pigment particles is determined with a Nicomp 30 Submicron Particle Analyzer based upon the principle of dynamic light scattering. The ink is diluted with ethyl acetate to a pigment concentration of 0.002 wt %.

However for a white UV curable ink, the numeric average particle diameter of the white pigment is preferably from 50 to 500 nm, more preferably from 150 to 400 nm, and most preferably from 200 to 350 nm. Sufficient hiding power cannot be obtained when the average diameter is less than 50 nm, and the storage ability and the jet-out suitability of the ink tend to be degraded when the average diameter exceeds 500 nm. The determination of the numeric average particle diameter is best performed by photon correlation spectroscopy at a wavelength of 633 nm with a 4 mW HeNe laser on a diluted sample of the pigmented inkjet ink. A suitable particle size analyzer used was a MALVERN™ nano-S available from Goffin-Meyvis. A sample can, for example, be prepared by addition of one drop of ink to a cuvet containing 1.5 mL ethyl acetate and mixed until a homogenous sample was obtained. The measured particle size is the average value of 3 consecutive measurements consisting of 6 runs of 20 seconds.

Suitable white pigments are given by Table 2 in [0116] of WO 2008/074548 (AGFA GRAPHICS). The white pigment is preferably a pigment with a refractive index greater than 1.60. The white pigments may be employed singly or in combination. Preferably titanium dioxide is used as pigment with a refractive index greater than 1.60. Suitable titanium dioxide pigments are those disclosed in [0117] and in [0118] of WO 2008/074548 (AGFA GRAPHICS).

The pigments are present in the range of 0.01 to 10% by weight, preferably in the range of 0.1 to 5% by weight, each based on the total weight of UV curable ink. For white UV curable inks, the white pigment is preferably present in an amount of 3% to 30% by weight of the ink composition, and more preferably 5% to 25%. An amount of less than 3% by weight cannot achieve sufficient covering power and usually exhibits very poor storage stability and ejection property.

Generally pigments are stabilized in the dispersion medium by dispersing agents, such as polymeric dispersants. However, the surface of the pigments can be modified to obtain so-called "self-dispersible" or "self-dispersing" pigments, i.e. pigments that are dispersible in the dispersion medium without dispersants.

Dispersants

The dispersant is preferably a polymeric dispersant. Typical polymeric dispersants are copolymers of two monomers but may contain three, four, five or even more monomers. The properties of polymeric dispersants depend on both the nature of the monomers and their distribution in the polymer. Suitable copolymeric dispersants have the following polymer compositions:

statistically polymerized monomers (e.g. monomers A and B polymerized into ABBAABAB);

alternating polymerized monomers (e.g. monomers A and B polymerized into ABABABAB);

gradient (tapered) polymerized monomers (e.g. monomers A and B polymerized into AAABAABBABBB);

block copolymers (e.g. monomers A and B polymerized into AAAAABBBBBB) wherein the block length of each of the blocks (2, 3, 4, 5 or even more) is important for the dispersion capability of the polymeric dispersant;

graft copolymers (graft copolymers consist of a polymeric backbone with polymeric side chains attached to the backbone); and mixed forms of these polymers, e.g. blocky gradient copolymers.

Suitable polymeric dispersants are listed in the section on "Dispersants", more specifically [0064] to [0070] and [0074] to [0077], in EP 1911814 A (AGFA GRAPHICS) incorporated herein as a specific reference.

The polymeric dispersant has preferably a number average molecular weight Mn between 500 and 30000, more preferably between 1500 and 10000.

The polymeric dispersant has preferably a weight average molecular weight Mw smaller than 100000, more preferably smaller than 50000 and most preferably smaller than 30000.

The polymeric dispersant has preferably a polydispersity PD smaller than 2, more preferably smaller than 1.75 and most preferably smaller than 1.5.

Commercial examples of polymeric dispersants are the following:

DISPERBYK™ dispersants available from BYK CHEMIE GMBH;
SOLSPERSE™ dispersants available from NOVEON;
TEGO™ DISPERS™ dispersants from EVONIK;
EDAPLAN™ dispersants from MÜNZING CHEMIE;
ETHACRYL™ dispersants from LYONDELL;
GANEX™ dispersants from ISP;
DISPEX™ and EFKA™ dispersants from CIBA SPECIALTY CHEMICALS INC;
DISPONER™ dispersants from DEUCHEM; and
JONCRYL™ dispersants from JOHNSON POLYMER.

Particularly preferred polymeric dispersants include SOLSPERSE™ dispersants from NOVEON, EFKA™ dispersants from CIBA SPECIALTY CHEMICALS INC and DISPERBYK™ dispersants from BYK CHEMIE GMBH. Particularly preferred dispersants are SOLSPERSE™ 32000, 35000 and 39000 dispersants from NOVEON.

The polymeric dispersant is preferably used in an amount of 2 to 600 wt %, more preferably 5 to 200 wt % based on the weight of the pigment.

Dispersion Synergists

A dispersion synergist usually consists of an anionic part and a cationic part. The anionic part of the dispersion synergist exhibiting a certain molecular similarity with the colour pigment and the cationic part of the dispersion synergist consists of one or more protons and/or cations to compensate the charge of the anionic part of the dispersion synergist.

The synergist is preferably added in a smaller amount than the polymeric dispersant(s). The ratio of polymeric dispersant/dispersion synergist depends upon the pigment and should be determined experimentally. Typically the ratio wt % polymeric dispersant/wt % dispersion synergist is selected between 2:1 to 100:1, preferably between 2:1 and 20:1.

Suitable dispersion synergists that are commercially available include SOLSPERSE™ 5000 and SOLSPERSE™ 22000 from NOVEON.

Particular preferred pigments for the magenta ink used are a diketopyrrolo-pyrrole pigment or a quinacridone pigment. Suitable dispersion synergists include those disclosed in EP 1790698 A (AGFA GRAPHICS), EP 1790696 A (AGFA GRAPHICS), WO 2007/060255 (AGFA GRAPHICS) and EP 1790695 A (AGFA GRAPHICS).

In dispersing C.I. Pigment Blue 15:3, the use of a sulfonated Cu-phthalocyanine dispersion synergist, e.g. SOLSPERSE™ 5000 from NOVEON is preferred. Suitable dispersion synergists for yellow inkjet inks include those disclosed in EP 1790697 A (AGFA GRAPHICS).

Surfactants

The radiation curable compositions and inks may contain a surfactant. The surfactant(s) can be anionic, cationic, non-ionic, or zwitter-ionic and are usually added in a total quantity less than 10 wt % based on the total weight of the radiation curable composition or ink and particularly in a total less than 5 wt % based on the total weight of the radiation curable composition or ink.

Suitable surfactants include those disclosed in paragraphs [0283] to [0291] of WO 2008/074548 (AGFA GRAPHICS) incorporated herein as a specific reference.

Inhibitors

The UV curable compositions and inks may contain a polymerization inhibitor. Suitable polymerization inhibitors include phenol type antioxidants, hindered amine light stabilizers, phosphor type antioxidants, hydroquinone monomethyl ether commonly used in (meth)acrylate monomers, and hydroquinone, t-butylcatechol, pyrogallol, 2,6-di-tert.butyl-4-methylphenol may also be used.

Suitable commercial inhibitors are, for example, SUMILIZER™ GA-80, SUMILIZER™ GM and SUMILIZER™ GS produced by Sumitomo Chemical Co. Ltd.; GENORAD™ 16, GENORAD™ 18 and GENORAD™ 20 from Rahn AG; IRGASTAB™ UV10 and IRGASTAB™ UV22, TINUVIN™ 460 and CGS20 from Ciba Specialty Chemicals; FLOORSTAB™ UV range (UV-1, UV-2, UV-5 and UV-8) from Kromachem Ltd, ADDITOL™ S range (S100, S110, S120 and S130) from Cytec Surface Specialties.

The inhibitor is preferably a polymerizable inhibitor.

Since excessive addition of these polymerization inhibitors may lower the curing speed, it is preferred that the amount capable of preventing polymerization is determined prior to blending. The amount of a polymerization inhibitor is preferably lower than 5 wt %, more preferably lower than 3 wt % of the total radiation curable composition or ink.

Preparation of Curable Inks

The average particle size and distribution of a colour pigment is an important feature for inkjet inks. The inkjet ink may be prepared by precipitating or milling the pigment in the dispersion medium in the presence of the dispersant.

Mixing apparatuses may include a pressure kneader, an open kneader, a planetary mixer, a dissolver, and a Dalton Universal Mixer. Suitable milling and dispersion apparatuses are a ball mill, a pearl mill, a colloid mill, a high-speed disperser, double rollers, a bead mill, a paint conditioner, and triple rollers. The dispersions may also be prepared using ultrasonic energy.

Many different types of materials may be used as milling media, such as glasses, ceramics, metals, and plastics. In a preferred embodiment, the grinding media can comprise particles, preferably substantially spherical in shape, e.g. beads consisting essentially of a polymeric resin or yttrium stabilized zirconium oxide beads.

In the process of mixing, milling and dispersion, each process is performed with cooling to prevent build up of heat, and as much as possible under light conditions in which actinic radiation has been substantially excluded.

The inkjet ink may contain more than one pigment, and may be prepared using separate dispersions for each pigment, or alternatively several pigments may be mixed and co-milled in preparing the dispersion.

The dispersion process can be carried out in a continuous, batch or semi-batch mode.

The preferred amounts and ratios of the ingredients of the mill grind will vary widely depending upon the specific materials and the intended applications. The contents of the milling mixture comprise the mill grind and the milling media. The mill grind comprises pigment, polymeric dispersant and a liquid carrier. For inkjet inks, the pigment is usually present in the mill grind at 1 to 50 wt %, excluding the milling media. The weight ratio of pigment over polymeric dispersant is 20:1 to 1:2.

The milling time can vary widely and depends upon the pigment, mechanical means and residence conditions selected, the initial and desired final particle size, etc. In a preferred embodiment of the present invention pigment dispersions with an average particle size of less than 100 nm may be prepared.

After milling is completed, the milling media is separated from the milled particulate product (in either a dry or liquid dispersion form) using conventional separation techniques, such as by filtration, sieving through a mesh screen, and the like. Often the sieve is built into the mill, e.g. for a bead mill. The milled pigment concentrate is preferably separated from the milling media by filtration.

In general it is desirable to make the inkjet inks in the form of a concentrated mill grind, which is subsequently diluted to the appropriate concentration for use in the inkjet printing system. This technique permits preparation of a greater quantity of pigmented ink from the equipment. By dilution, the inkjet ink is adjusted to the desired viscosity, surface tension, colour, hue, saturation density, and print area coverage for the particular application.

EXAMPLES

Materials

All materials used in the following examples were readily available from standard sources such as ALDRICH CHEMICAL Co. (Belgium) and ACROS (Belgium) unless otherwise specified. The water used was deionized water.

DPGDA is dipropyleneglycoldiacrylate from SARTOMER. TMPTA is trimethylolpropane triacrylate available as SARTOMER™ SR351 from SARTOMER. VEEA is 2-(vinylethoxy)ethyl acrylate, a difunctional monomer available from NIPPON SHOKUBAI, Japan.

EPD is ethyl 4-dimethylaminobenzoate, available under the trade name of Genocure™ EPD from RAHN AG. IC127 is an abbreviation used for IRGACURE™ 127, supplied by Ciba Specialty Chemicals:

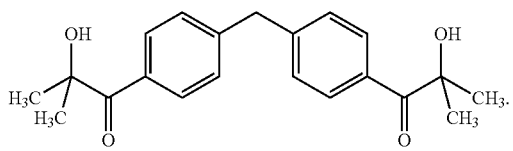 [SMILES: CC(C)(O)C(=O)c1ccc(Cc2ccc(C(=O)C(C)(C)O)cc2)cc1]

IC907 is an abbreviation used for IRGACURE™ 907 is 2-methyl-1-[4-(methylthio)phenyl]-2-morpholino-propan-1-one, a photoinitiator available from CIBA SPECIALTY CHEMICALS.

IC379 is an abbreviation used for IRGACURE™ 379 is a photoinitiator available from CIBA SPECIALTY having as chemical structure:

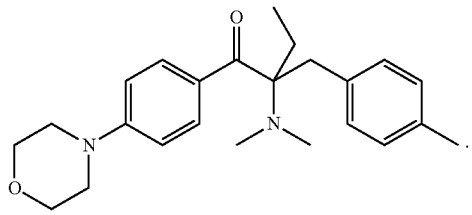 [SMILES: CCC(Cc1ccc(C)cc1)(C(=O)c1ccc(N2CCOCC2)cc1)N(C)C]

ITX is an abbreviation used for DAROCUR™ ITX, an isomeric mixture of 2- and 4-isopropylthioxanthone from CIBA SPECIALTY CHEMICALS.

TPO is an abbreviation used for 2,4,6-trimethylbenzoyl-diphenyl-phosphineoxide available under the trade name DAROCUR™ TPO from CIBA SPECIALTY CHEMICALS.

GENORAD™ 16 is a polymerization inhibitor from RAHN AG.

GENOSOL is a 50 wt % solution of GENORAD™ 16 in DPGDA.

PB15:4 is an abbreviation used for HOSTAPERM™ Blue P-BFS, a cyan pigment (C.I. Pigment Blue 15:4) available from CLARIANT.

DB162 is an abbreviation used for the polymeric dispersant DISPERBYK™ 162 available from BYK CHEMIE GMBH whereof the solvent mixture of 2-methoxy-1-methylethylacetate, xylene and n-butylacetate was removed.

DB162sol is a 30 wt % solution of DB162 in DPGDA.

S35000 is an abbreviation used for SOLSPERSE™ 35000, a polyethyleneimine-polyester hyperdispersant from NOVEON.

S35000SOL is a 40 wt % solution of S35000 in DPGDA.

BYK™ UV3510 is a polyether modified polydimethylsiloxane wetting agent available from BYK CHEMIE GMBH.

Measurement Methods

1. Curing Speed

The curing speed on a Fusion DRSE-120 conveyor was defined as the percentage of the maximum output of the lamp needed to cure the samples. The lower the number the higher curing speed. A sample was considered as fully cured at the moment scratching with a Q-tip caused no visual damage.

A percentage of more then 100% of the maximum output of the lamp means that the speed of the conveyor belt had to be reduced to get the sample fully cured at the maximum output of the lamp. The higher the percentage, the more the belt had to be slowed down. A curing speed of 160% means a belt speed of 12.5 m/min at the maximum output of the lamp. A percentage between 150% and 200% is considered as at the edge of practical use. A percentage above 200% is considered out of the range for practical use and no higher percentages are measured.

2. Curing Degree

The curing degree was tested on a coating immediately after curing with UV light. The cured coating is rubbed with the means of a Q-tip. When the surface is not damaged, the coating is fully cured. When some of the cured coating can be damaged, the coating is only partly cured. When the whole cured coating is damaged, the coating is not cured.

3. Average Particle Size

The particle size of pigment particles in an inkjet ink was determined by photon correlation spectroscopy at a wavelength of 633 nm with a 4 mW HeNe laser on a diluted sample of the pigmented inkjet ink. The particle size analyzer used was a MALVERN™ nano-S available from Goffin-Meyvis.

The sample was prepared by addition of one drop of ink to a cuvette containing 1.5 mL ethyl acetate and mixed until a homogenous sample was obtained. The measured particle size is the average value of 3 consecutive measurements consisting of 6 runs of 20 seconds. For good ink jet characteristics (jetting characteristics and print quality) the average particle size of the dispersed particles is below 200 nm, preferably between 70 and 150 nm.

4. Image Tone

Printed or coated samples were measured with a spectrophotometer (GRETAG SPM, manufactured by GRETAG INC.) to determine the coordinates of the L*a*b* colours system of the colour difference indication method specified in CIE (Commission International de l'Eclairage). In this case, the measurement was carried out under conditions of light source D50, provision of no light source filter, absolute white as reference white, and angle of visibility 2°.

5. Degree of Conversion

The degree of conversion, i.e. the percentage of converted functional groups, may be determined by for example RT-FTIR (Real-Time Fourier Transform Infra-Red Spectroscopy).

From a radiation curable composition, an FTIR-spectrum, using a micro-ATR method on a BIO-RAD FTS-7 spectrometer, equipped with a split pea module from Harrick, was taken before curing, by applying a drop of ink on the split pea module. A second sample of the radiation curable composition was coated on a PGA-paper, using a bar coater and a 10 μm wired bar. The coated sample was mounted on a belt, transporting the samples under a Phoseon 4W 395 nm LED at a speed specified in the examples.

After coating and curing the radiation curable composition as described above, a second FTIR-spectrum was taken from each coated and cured sample under the same conditions. The change in peak height at 810 cm$^{-1}$, corresponding to a C—H vibration on the double bonds was measured relative to the C=O-stretching vibration at 1728 cm$^{-1}$, which was used as an internal reference and the following two ratios were determined:

$$\text{ratio}_{curing} = I_{810}((curing))/I_{1728}((curing))$$

$$\text{ratio}_{ref} = I_{810}(ref)/I_{1728}(ref)$$

wherein I corresponds to the respective peak heights. It was assumed that the ester function remained unchanged during curing. The curing percentage was calculated as follows:

$$\text{Curing \%} = 100 - (\text{ratio}_{curing}/\text{ratio}_{ref})*100$$

A full cure is defined as a degree of conversion wherein the increase in the percentage of converted functional groups, with increased exposure to radiation (time and/or dose), is negligible. A full cure corresponds with a conversion percentage that is within 10%, preferably 5%, from the maximum conversion percentage defined by the horizontal asymptote in the RT-FTIR graph (percentage conversion versus curing energy or curing time).

Example 1

This example illustrates the simplicity of the method for preparing a photoinitiator according to a preferred embodiment of the present invention.

Photoinitiator INI-1

First, 9-(2-Ethyl-hexyl)-9H-carbazole was synthesized according to the following synthesis scheme:

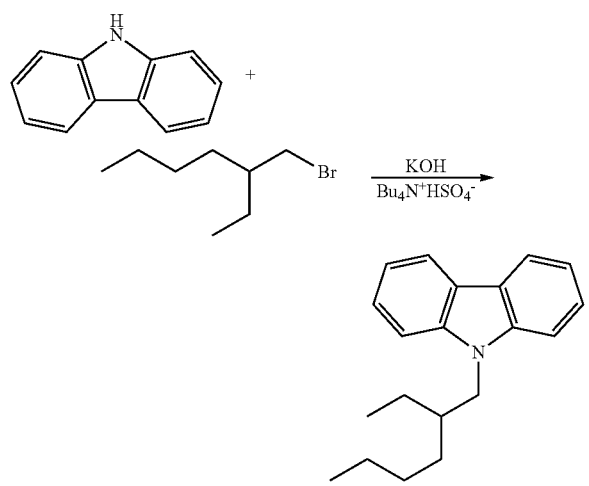

To a pale brown solution of 9H-carbazole (66.9 g, 0.4 mol), 3-bromomethyl-heptane (125.5 g, 0.65 mol) and tetrabutylammonium hydrogensulfate (37.3 g, 0.11 mol) in acetone (650 ml), potassium hydroxide (86%) (49.6 g, 0.76 mol) was added in portions. The reaction mixture was heated to reflux temperature and stirred for about 16 hours. The inorganic residues were removed by filtration and the solvent was evaporated under reduced pressure. The residual oil was dissolved in methyl-tert-butylether (500 ml) and extracted with distilled water (500 ml). The aqueous layer was extracted with dichloromethane (350 ml).

The pooled organic fractions were dried over $MgSO_4$ and the solvent was evaporated under reduced pressure to obtain a brown oil. The crude 9-(2-ethyl-hexyl)-9H-carbazole was purified on a Merck SVP D40 Column using n-hexane as eluent. Evaporation of the pooled fractions yielded 85 g of 9-(2-Ethyl-hexyl)-9H-carbazole.

Then, 2[6-Ethoxyoxalyl-9-(2-ethyl-hexyl)-9H-carbazol-3-yl]-oxo-acetic acid ethyl ester was synthesized according to the following synthesis scheme:

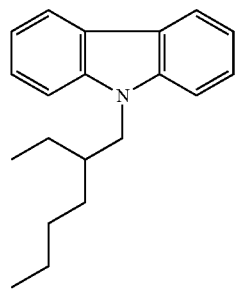

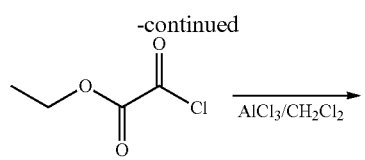

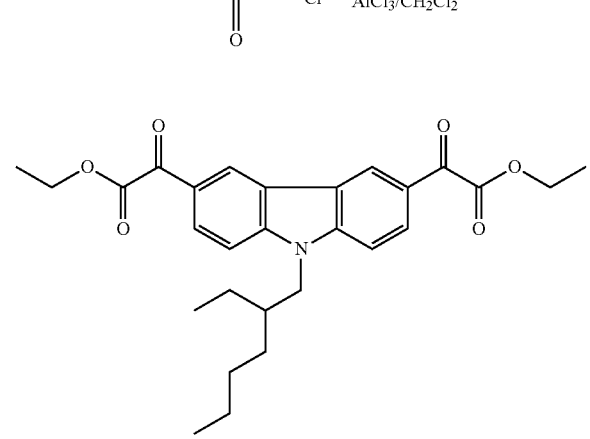

To a solution of 9-(2-ethyl-hexyl)-9H-carbazole (7.0 g, 0.025 mol) in dichloromethane (30 ml), ethyloxalyl chloride (7.2 g, 0.0525 mol) was added and stirred for 15 minutes at room temperature. The reaction mixture was cooled to −5° C. and aluminium chloride (7.3 g, 0.055 mol) was added in portions while the temperature was maintained below 0° C. The reaction mixture was allowed to stir at room temperature for 1.5 hours. The reaction mixture was poured into ice (200 g) and diluted with dichloromethane (100 ml). The organic layer was separated and extracted 5 times with distilled water (150 ml). The organic layer was dried over $MgSO_4$, filtered and the solvent was removed under reduced pressure. The residual oil was purified on a Prochrom LC80 Column using dichloromethane as eluent. Evaporation of the pooled fractions yielded 4.3 g of INI-1. ($R_f$:0.25, eluent 100% methylene chloride, Merck Kieselgel 60 $F_{254}$)

Photoinitiator INI-2

First, [9-(2-ethyl-hexyl)-9H-carbazol-3-yl]-phenylmethanone was synthesized according to the following synthesis scheme:

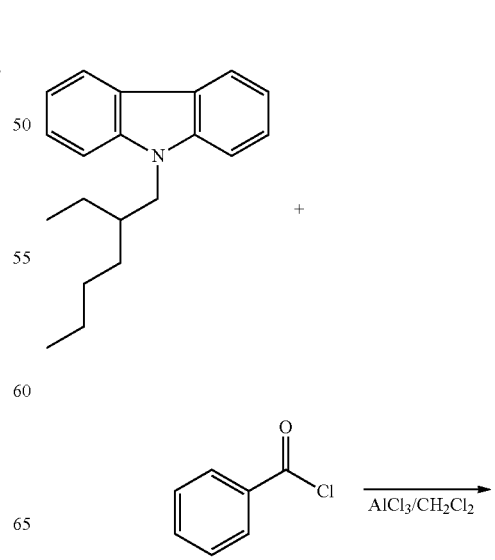

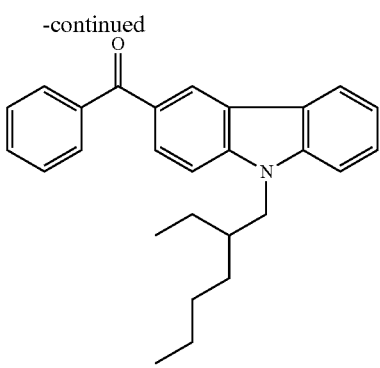

To a solution of 9-(2-ethyl-hexyl)-9H-carbazole (7.0 g, 0.025 mol) in dichloromethane (30 ml), benzoyl chloride (4.5 g, 0.0525 mol) was added and stirred for 15 minutes at room temperature. Aluminium chloride (7.3 g, 0.055 mol) was added in portions while the temperature was maintained below 30° C. The reaction mixture was allowed to stir at room temperature for 15 hours. The reaction mixture was poured into ice (150 g) and distilled water (100 ml) and diluted with dichloromethane (200 ml). The organic layer was separated and washed with a saturated solution of sodium bicarbonate (250 ml) and a saturated solution of sodium chloride (250 ml). The organic layer was dried over $MgSO_4$, filtered and the solvent was removed under reduced pressure. The residual solid was purified on a Prochrom LC80 Column using ethyl acetate/n-hexane (20/80) as eluent. TLC shows a yellow fluorescent product with Rf-value of 0.48 in dichloromethane as eluent. Evaporation of the pooled fractions yielded 1.5 g of [9-(2-ethyl-hexyl)-9H-carbazol-3-yl]-phenyl-methanone.

Then, [6-benzoyl-9-(2-ethyl-hexyl)-9H-carbazol-3-yl]-oxo-acetic acid ethyl ester was synthesized according to the following synthesis scheme:

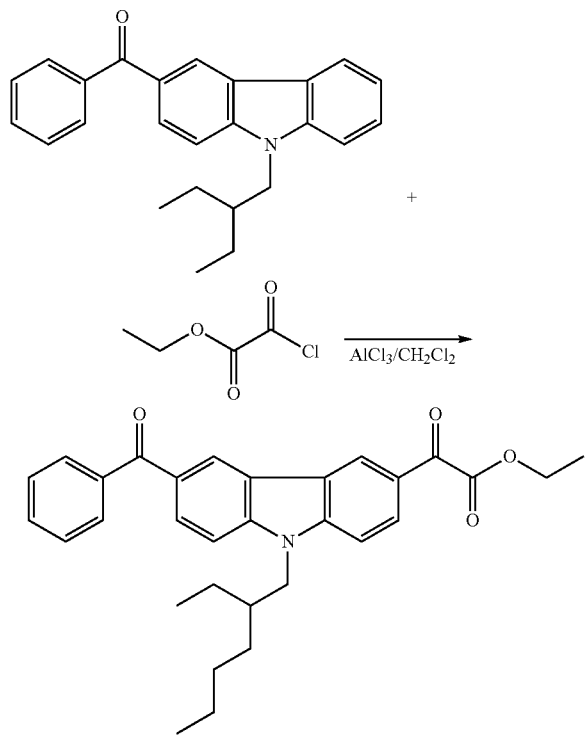

To a solution of [9-(2-ethyl-hexyl)-9H-carbazole-3-yl]-phenyl-methanone (4.4 g, 0.011 mol) in dichloromethane (40 ml), ethyloxalyl chloride (4.3 g, 0.03135 mol) was added and stirred for 15 minutes at room temperature. Aluminium chloride (4.2 g, 0.03135 mol) was added in portions while the temperature was maintained below 30° C. The reaction mixture was allowed to stir at room temperature for 48 hours. The reaction mixture was poured into ice (100 g) and distilled water (50 ml) and diluted with dichloromethane (60 ml). The organic layer was separated, dried over $MgSO_4$ and filtered. The solvent was removed under reduced pressure. The residue was purified on a Prochrom LC80 Column using dichloromethane as eluent. Evaporation of the pooled fractions yielded 3.6 g of INI-2 ($R_f$:0.28, eluent:100% methylene chloride, Merck Kieselgel 60 $F_{254}$).

Photoinitiators INI-3

[9-(2-ethyl-hexyl)-9H-carbazol-3-yl]-oxo-acetic acid ethyl ester was synthesized according to the following synthesis scheme:

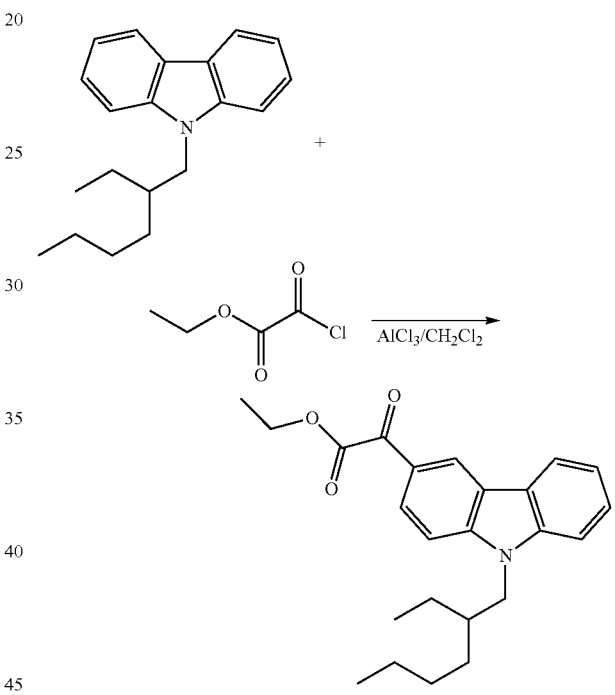

To a solution of 9-(2-ethyl-hexyl)-9H-carbazole (7.0 g, 0.025 mol) in dichloromethane (30 ml), chloro-oxo-acetic acid ethyl ester (7.2 g, 0.0525 mol) was added and stirred for 15 minutes at room temperature. The reaction mixture was cooled to −5° C. and aluminium chloride (7.3 g, 0.055 mol) was added in portions while the temperature was maintained below 0° C. The reaction mixture was allowed to stir at room temperature for 90 minutes. The reaction mixture was poured into ice (200 g) and diluted with dichloromethane (100 ml). The organic layer was separated and washed five times with distilled water (150 ml). The organic layer was dried over $MgSO_4$ and filtered. The solvent was removed under reduced pressure. The residual oil was purified on a Prochrom LC80 using dichloromethane as eluent. Evaporation of pooled fractions yielded 3.8 g of INI-3 ($R_f$:0.6, eluent:100% methylene chloride, Merck Kieselgel 60 $F_{254}$).

Photoinitiators INI-6 and INI-20

[9-6-(2-ethyl-hexyloxyoxalyl)-9H-carbazol-3-yl)-oxo-acetic acid 2-ethyl-hexyl ester was synthesized according to the following synthesis scheme:

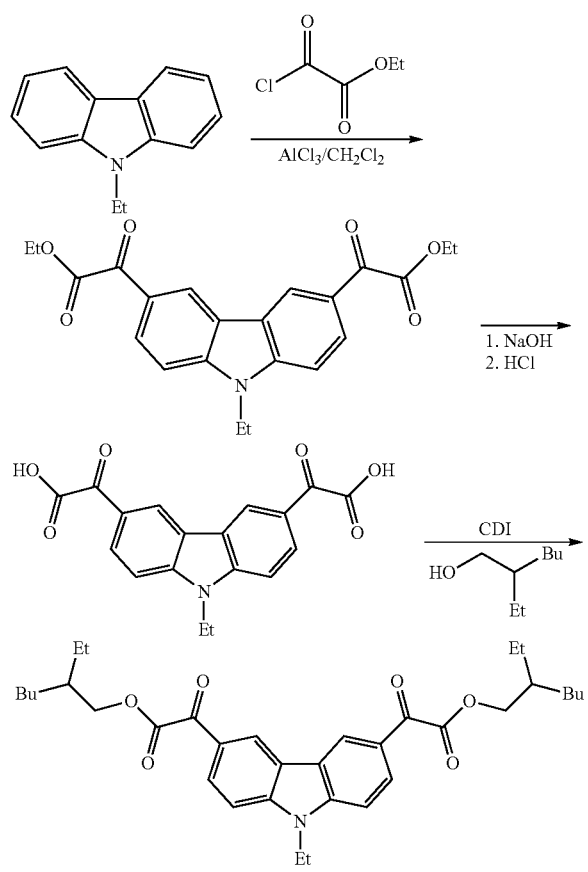

The Friedel-Crafts-acylation:

60 g (0.307 mol) of 9-ethyl-carbazole (supplied by Aldrich) was dissolved in 250 ml methylene chloride. 92.3 g (0.676 mol) ethyl-oxalyl chloride was added. 90 g (0.676 mol) aluminium chloride was added portion wise, while maintaining the temperature below 35° C. Upon complete addition, the reaction mixture was cooled to −10° C. and the reaction was allowed to continue for 24 hours. The reaction mixture became difficult to stir. 350 ml ethyl acetate was added at room temperature and the reaction mixture was stirred for 16 hours. The reaction mixture was poured into 360 g ice and an additional 360 ml ethyl acetate was added. The organic fraction was isolated, extracted with brine and twice with 200 ml of a saturated NaHCO$_3$ solution. The intermediate diester precipitated from the organic fraction and was isolated by filtration. The filtrate was evaporated under reduced pressure and the residue was treated with toluene, yielding a second crop of the diester. The fractions were pooled and 52.8 g (43.6%) of the diester was isolated (R$_f$: 0.23, eluent 70/30 hexane/ethyl acetate on Merck Kieselgel 60 F$_{254}$.). The intermediate was used without further purification.

The hydrolysis of the esters:

42.8 g (0.108 mol) of the diester was dissolved in 150 ml ethanol. 13 g (0.322 mol) NaOH was added and the reaction mixture was heated to 60° C. The reaction was allowed to continue for one hour at 60° C. 100 ml water was added to the reaction mixture and the mixture was acidified to pH=1, using a 6N hydrochloric acid solution. The dicarboxylic acid precipitated from the medium, was isolated by filtration and dried. 18.7 g (52%) of the dicarboxylic acid was isolated. LCMS analysis indicated a purity of 95%. The dicarboxylic acid was used without further purification.

The CDI-coupling:

7.5 g (22 mmol) of the dicarboxylic acid was dissolved in 20 ml dimethyl acetamide. 6.9 g (41 mmol) CDI was added. The temperature rose to 35° C. and the reaction was allowed to continue for 4 hours at 80° C. 5.8 g (44 mmol) 2-ethy-hexyl alcohol was added and the reaction was allowed to continue for one hour at 80° C. After one hour, an additional 5.8 g (44 mmol) 2-ethyl-hexyl alcohol was added and the reaction was allowed to continue at 80° C. for 16 hours. After cooling down to room temperature, 150 ml methyl tert.butyl ether and 100 ml water were added to the reaction mixture. The aqueous layer was extracted three times with 100 ml methyl tert.butyl ether. The organic fractions were pooled, dried over MgSO$_4$ and evaporated under reduced pressure. INI-6 was isolated by preparative column chromatography on a Prochrom LC80 column, using Kromasil Si 60A 10 μm and a gradient elution from 100% methylene chloride to methylene chloride/ethyl acetate 94/6 at a flow rate of 150 ml/min. (R$_f$:0.35, eluent MeOH/NaCl 90/10, Partisil KC18F).

INI-20 was isolated as side product in this reaction. (R$_f$: 0.25, eluent MeOH/0.5 M NaCl 90/10, Partisil KC18F).

Photoinitiators INI-4 and INI-19 (9-sec.butyl-6-ethoxyoxalyl-9H-carbazol-3-yl)-oxo-acetic acid ethyl ester (INI-5) and (9-sec.butyl-9H-carbazol-3-yl)-oxo-acetic acid ethyl ester (INI-10) were synthesized according to the following synthesis scheme:

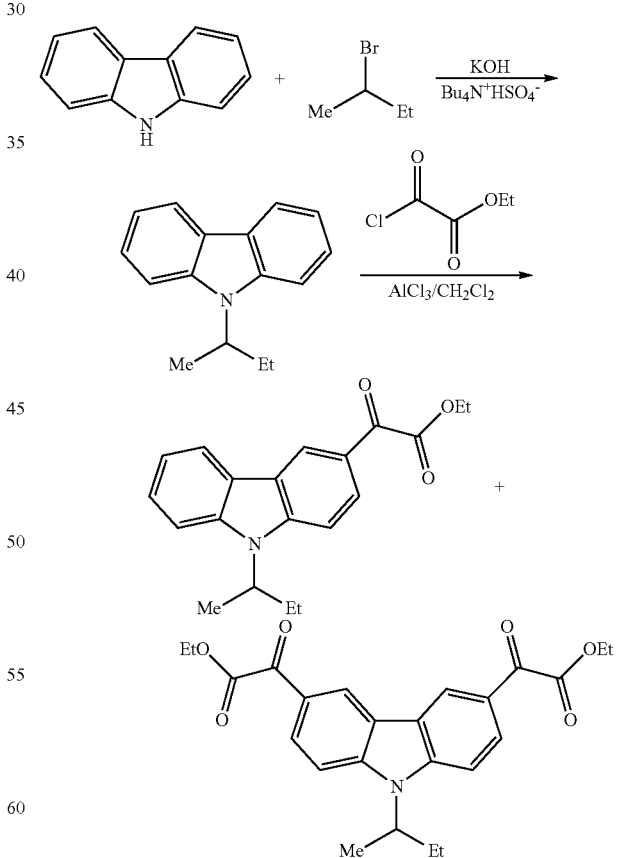

Alkylation of Carbazole:

25 g (0.15 mol) of carbazole and 33 g (0.24 mol) 2-bromobutane were dissolved in 250 ml acetone. 14 g (40 mmol) tetrabutylammonium hydrogen sulfate was added, followed by the addition of 18.6 g (0.285 mol) potassium hydroxide (88%). The reaction mixture was refluxed for 10 hours. After 10 hours, an additional 4 g (30 mmol) 2-bromo-butane and 2 g (31 mmol) potassium hydroxide (88%) were added and the reaction was allowed to continue at reflux temperature for 16 hours. The precipitated salts were removed by filtration and the solvent was evaporated under reduced pressure. The residue was redissolved in 200 ml methyl tert.butyl ether and extracted with 100 ml 1M $Na_2CO_3$ and 100 ml water. The organic fraction was isolated, dried over $MgSO_4$ and evaporated under reduced pressure. N-sec.butyl-carbazole was isolated by preparative column chromatography on a Prochrom LC80 column, using Kromasil Si60 10 μm and n. hexane/methylene chloride 93/7 as eluent. 8.7 g (26%) of N-sec.butyl carbazole was isolated.

Friedel-Crafts Acylation:

8.24 g (37 mmol) of N-sec.butyl-carbazole was dissolved in 50 ml methylene chloride. 10.6 g (78 mmol) ethyl-oxalyl chloride was added and the reaction mixture was cooled to −15° C. 10.9 g (82 mmol) aluminium chloride was added portion wise, while the temperature was kept at −5° C. The reaction was allowed to continue for 10 minutes at −5° C. The reaction was further allowed to continue for 45 minutes at room temperature. The reaction mixture was poured into 300 ml ice. 100 ml methylene chloride was added. The organic fraction was isolated, dried over $MgSO_4$ and evaporated under reduced pressure. Both INI-4 and INI-19 were isolated by preparative column chromatography on a Prochrom LC80 column, using Kromasil Si60A 10 μm and n.-hexane/ethyl acetate 70/30 as eluent. 5.4 g of INI-19 was isolated ($R_f$:0.51, eluent ethyl acetate/hexane 30/70, Merck Kieselgel $60F_{254}$). 3.57 g of INI-4 was isolated ($R_f$:0.3, eluent ethyl acetate/hexane 30/70, Merck Kieselgel $60F_{254}$).

Photoinitiator INI-16

Acrylic acid 4-(3-(2-[6-benzoyl-9-(2-ethyl-hexyl)-9H-carbazol-3-yl]-2-oxo-acetoxy)-2-hydroxy-propoxy)-butyl ester was synthesized according to the following synthesis scheme:

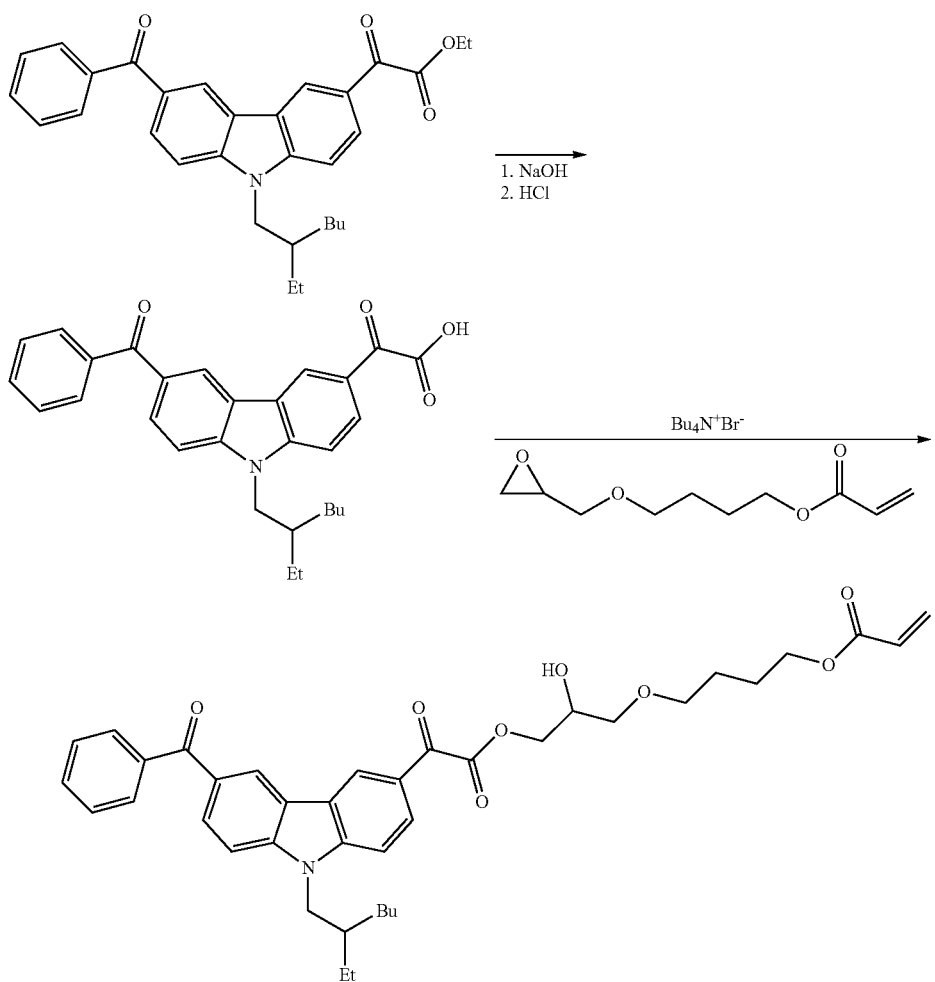

Hydrolysis of INI-2:

2.2 g (4.6 mmol) of INI-2 was dissolved in 20 ml ethanol. The reaction mixture was heated to 50° C. and 0.46 ml of a 10 N NaOH solution (4.6 mmol) was added. The reaction was allowed to continue for three hours at 50° C. The solvent was removed under reduced pressure and the residue was dissolved in 10 ml water. The mixture was acidified with a 6N hydrochloric acid solution. The mixture was extracted with 20 ml methyl tert.butyl ether. The organic fraction was isolated, dried over $MgSO_4$ and evaporated under reduced pressure. 2.1 g of the intermediate carboxylic acid was isolated. The intermediate was used without further purification.

Reaction with the Epoxy-Acrylate:

2 g (4.4 mmol) of the intermediate carboxylic acid was dissolved in 20 ml acetonitrile. 10 mg BHT and 0.14 g (0.44 mmol) tetrabutylammonium bromide were added and the mixture was heated to reflux. 0.9 g (4.4 mmol) of 4-(glycidyloxy)butyl acrylate was added and the reaction was allowed to continue for 16 hours at reflux temperature. The solvent was removed under reduced pressure and INI-16 was purified by preparative column chromatography.

Photoinitiator INI-8

INI-8 was synthesized according to the following synthesis scheme:

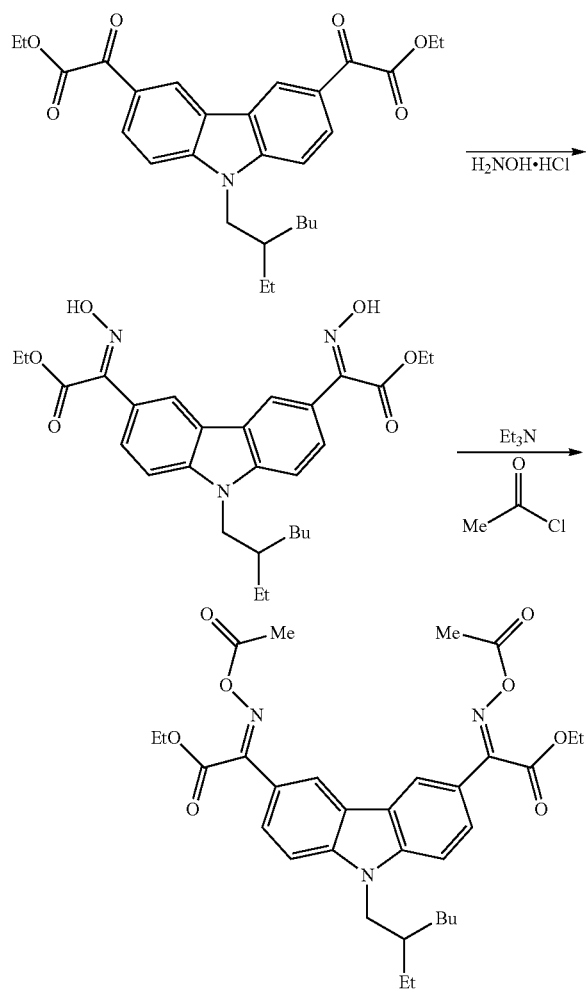

Synthesis of the Oximes:

3.8 g (7.9 mmol) of INI-1 was dissolved in 34 ml pyridine and 22 ml ethanol. 1.2 g (16.7 mmol) hydroxyl amine chlorohydrate was added and the reaction mixture was refluxed for 16 hours. An additional 1.2 g (16.7 mmol) hydroxyl amine chlorohydrate was added and the reaction was allowed to continue for an additional three hours at reflux temperature. The solvent was evaporated under reduced pressure and the residue was dissolved in 100 ml methylene chloride. The mixture was extracted with 100 ml 1 N hydrochloric acid and twice with 100 ml water. The organic fraction was isolated, dried over $MgSO_4$ and evaporated under reduced pressure. The intermediate oxime was isolated by preparative column chromatography on a Prochrom LC80 column, using Kromasil Si 60A 10 μm and a gradient elution from n.-hexane/ethyl acetate 70/30 to n.-hexane/ethyl acetate 50/50 at a flow rate of 150 ml/min. 1.4 g of the intermediate bis-oxime was isolated ($R_f$:0.5, eluent n.-hexane/ethyl acetate 50/50, Merck Kieselgel 60 $F_{254}$).

Acylation of the Oximes:

1.2 g (2.36 mmol) of the intermediate oxime was dissolved in 20 ml methylene chloride. 0.72 ml (5.19 mmol) triethyl amine was added, followed by the addition of 0.41 g (5.19 mmol) acetyl chloride. The reaction was allowed to continue for 16 hours at room temperature. The reaction mixture was extracted with 50 ml water, dried over $MgSO_4$ and evaporated under reduced pressure. INI-8 was purified by crystallisation from n.-hexane/ethyl acetate 60/40 ($R_f$:0.25, eluent:n.-hexane/ethyl acetate 50/50, Merck Kieselgel 60 $F_{254}$).

Example 2

This example illustrates the need for introducing a branched substituent on the nitrogen of the carbazole photoinitiators according to a preferred embodiment of the present invention and further illustrates their high photoreactivity and excellent yellowing behaviour.

Preparation of Concentrated Pigment Dispersions DISP-1 and DISP-2

Concentrated Pigment Dispersions DISP-1:

45,000 g of DB162sol and 450 g of GENOSOL were dissolved in 31,050 g of DPGDA in a vessel of 125 L using a DISPERLUX™ disperser (from DISPERLUX S.A.R.L., Luxembourg). 13,500 g of cyan pigment PB15:4 was added to the solution and stirred for 30 minutes. The vessel was then connected to a Netzsch LMZ10 mill having an internal volume of 10 L filled for 52% with 0.4 mm yttrium stabilized zirconia beads ("high wear resistant zirconia grinding media" from TOSOH Co.). The mixture was circulated over the mill for 7 hours and 45 minutes at a flow rate of about 2 L per minute and a rotation speed in the mill of about 15 m/s. During the complete milling procedure the content in the mill was cooled to a temperature of 42° C. After milling, the concentrated pigment dispersion DISP-1 was discharged into another 125 L vessel. The resulting concentrated pigment dispersion DISP-1 according to Table 2 exhibited an average particle size of 110 nm.

TABLE 2

| Component | wt % |
|---|---|
| PB15:4 | 15 |
| DB162 | 15 |
| Genorad ™ 16 | 1 |
| DPGDA | 69 |

Concentrated Pigment Dispersions DISP-2:

15,000 g of S35000sol and 300 g of GENOSOL were dissolved in 8,850 g of DPGDA in a vessel of 60 L. 6,000 g of cyan pigment PB15:4 was added to the solution and stirred for 30 minutes using a DISPERLUX™ disperser (from DISPERLUX S.A.R.L., Luxembourg). The vessel was then connected to a Bachofen DYNOMILL ECM POLY mill having an internal volume of 8.2 L filled for 42% with 0.4 mm yttrium stabilized zirconia beads ("high wear resistant zirconia grinding media" from TOSOH Co.). The mixture was circulated over the mill for 1 hour and 50 minutes at a flow rate of about 5 L per minute and a rotation speed in the mill of about 15 m/s. During the complete milling procedure the content of the mill was cooled to a temperature of 54° C. The concentrated pigment dispersion DISP-2 was discharged into another 60 L vessel. The resulting concentrated pigment dispersion DISP-2 according to Table 3 exhibited an average particle size of 119 nm.

TABLE 3

| Component | wt % |
|---|---|
| PB15:4 | 20 |
| S35000 | 20 |
| Genorad ™ 16 | 1 |
| DPGDA | 59 |

Preparation of Comparative Photoinitiator COMPINI-1

(6-Ethoxyoxalyl-9-ethyl-9H-carbazol-3-yl)-oxo-acetic acid ethyl ester was synthesized according to the following synthesis scheme:

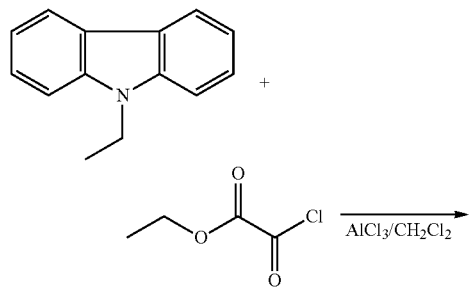

To a dark brown solution of 9-ethylcarbazole (14.6 g, 0.075 mol) in dichloromethane (100 ml), ethyloxalyl chloride (22.5 g, 0.0165 mol) was added and stirred for 15 minutes at room temperature. Aluminium chloride (22.0 g, 0.0165 mol) was added in portions while the temperature was maintained below 30° C. The reaction mixture was allowed to stir at room temperature for 24 hours. Ethyl acetate was added (150 ml), and the mixture was again stirred for 24 hours at room temperature. The reaction mixture was diluted with ethyl acetate (600 ml) and poured into ice (250 g) and distilled water (250 ml).

After stirring for 1 hour, the organic layer was separated and washed once with a saturated solution of sodium bicarbonate (150 ml) and once with a saturated solution of sodium chloride (300 ml). The organic layer was separated, dried on $MgSO_4$ and the solvent was evaporated under reduced pressure to obtain a yellow solid. The residue was dissolved in dichloromethane (36 ml) and n-hexane (100 ml) was added. The crude (6-ethoxyoxalyl-9-ethyl-9H-carbazol-3-yl)-oxoacetic acid ethyl ester precipitated from the medium and was isolated by filtration. The crude (6-ethoxyoxalyl-9-ethyl-9H-carbazol-3-yl)-oxo-acetic acid ethyl ester was purified on a Merck SVP D40 Column using n-hexane/dichloromethane (50/50) as eluent. After evaporation of the pooled fractions, the residue was dissolved in dichloromethane and n-hexane was added. Crystallization provided 7.4 g of COMPINI-1. ($R_f$ 0.25, eluent:n.-hexane/ethyl acetate 70/30, Merck Kieselgel 60 $F_{254}$)

Preparation of Radiation Curable Compositions

The comparative radiation curable compositions COMP-1 to COMP-4 and the inventive radiation curable compositions INV-1 to INV-4 were prepared according to Table 4. The weight % (wt %) was based on the total weight of the radiation curable compositions.

TABLE 4

| wt % of | INV-1 | INV-2 | INV-3 | INV-4 | COMP-1 | COMP-2 | COMP-3 | COMP-4 |
|---|---|---|---|---|---|---|---|---|
| DPGDA | — | 64.6 | — | 66.6 | — | 69.0 | — | 66.3 |
| VEEA | 24.5 | — | 26.5 | — | 30.0 | — | 26.2 | — |
| TMPTA | 38.6 | — | 38.6 | — | 40.0 | — | 38.6 | — |
| GENORAD ™ 16 | 0.8 | 0.8 | 0.8 | 0.9 | 0.9 | 0.9 | 0.8 | 0.8 |
| EPD | 2.5 | 5.0 | 2.5 | 5.0 | 2.5 | 5.0 | 2.5 | 5.0 |
| ITX | — | — | — | — | 2.5 | 5.0 | — | — |
| TPO | — | 5.0 | — | 5.0 | — | 5.0 | — | 5.0 |
| IC907 | 4.0 | — | 4.0 | — | 4.0 | — | 4.0 | — |
| INI-1 | 9.5 | 9.5 | — | — | — | — | — | — |
| INI-3 | — | — | 7.5 | 7.5 | — | — | — | — |
| COMPINI-1 | — | — | — | — | — | — | 7.8 | 7.8 |
| DISP-1 | 20.0 | — | 20.0 | — | 20.0 | — | 20.0 | — |
| DISP-2 | — | 15.0 | — | 15.0 | — | 15.0 | — | 15.0 |
| BYK ™ UV3510 | 0.1 | 0.1 | 0.1 | 0.1 | 0.1 | 0.1 | 0.1 | 0.1 |

-continued

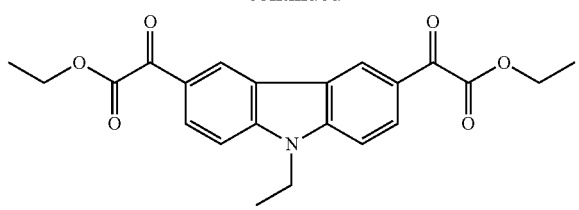

The comparative radiation curable compositions COMP-3 and COMP-4 could not be formulated due to insolubility of the carbazole based initiator COMPINI-1. Introducing a branched alkyl chain as in INI-1 and INI-3 resulted in initiators having a high compatibility with radiation curable compositions.

The comparative radiation curable compositions COMP-1 and COMP-2 and inventive radiation curable compositions INV-1 to INV-4 were coated on PGA-paper, using a bar coater and a 10 μm wired bar. The coated samples were mounted on a belt, transporting the samples under a Phoseon 4W 395 nm LED. The number of passes at a given belt speed to completely cure the samples was determined. The Q-tip method was used to determine complete cure. The results are summarized in Table 5.

TABLE 5

| Radiation Curable Composition | # passes at 5 m/min | # passes at 30 m/min |
|---|---|---|
| INV-1 | 1 | 2 |
| INV-2 | 1 | 4 |
| INV-3 | 2 | 6 |
| INV-4 | 2 | 6 |
| COMP-1 | 1 | 4 |
| COMP-2 | 1 | 4 |

The radiation curable compositions INV-1 to INV-4 and COMP-2 were cured on a Fusion DRSE-120 conveyor equipped with Fusion VPS/1600 lamp at 20 m/min at full power of the lamp. A second sample was cured with a Phoseon 4W 395 nm LED, passing the sample 4 times under the LED at a speed of 5 m/min. The stability of the image tone under both curing conditions was quantified by measuring the shift in b-value between the freshly printed sample and the sample stored for 7 days at ambient temperature. The results are summarized in Table 6.

TABLE 6

| Radiation curable sample | Δb (Fusion) | Δb (LED) |
|---|---|---|
| INV-1 | 1.5 | 2.72 |
| INV-2 | 2 | 3.15 |
| INV-3 | 0.93 | 2.4 |
| INV-4 | 1.55 | 2.31 |
| COMP-2 | 3.35 | 5.7 |

From Table 6, it becomes apparent that the radiation curable compositions according to preferred embodiments of the present invention have a significantly more stable yellowing behaviour in comparison with thioxanthones.

Example 3

This example illustrates the high curing speed of radiation curable inkjet inks according to a preferred embodiment of the present invention.

Preparation of Radiation Curable Inkjet Inks

The comparative radiation curable compositions COMP-5 and COMP-6 and the inventive radiation curable compositions INV-5 to INV-7 were prepared according to Table 7. The weight % (wt %) was based on the total weight of the radiation curable compositions.

TABLE 7

| wt % of | INV-5 | INV-6 | INV-7 | COMP-5 | COMP-6 |
|---|---|---|---|---|---|
| DPGDA | — | 70.5 | 64.6 | — | 69.0 |
| VEEA | 24.5 | — | — | 30.0 | — |
| TMPTA | 38.6 | — | — | 40.0 | — |
| GENORAD™ 16 | 0.8 | 0.9 | 0.8 | 0.9 | 0.9 |
| EPD | 2.5 | 2.5 | 5.0 | 2.5 | 5.0 |
| ITX | — | — | — | 2.5 | 5.0 |
| TPO | — | — | 5.0 | — | 5.0 |
| IC907 | 4.0 | 4.0 | — | 4.0 | — |
| IC379 | — | 3.0 | — | — | — |
| INI-2 | 9.5 | 4.0 | 9.5 | — | — |
| DISP-1 | 20.0 | — | — | 20.0 | — |
| DISP-2 | — | 15.0 | 15.0 | — | 15.0 |
| BYK™ UV3510 | 0.1 | 0.1 | 0.1 | 0.1 | 0.1 |

The compositions INV-5 to INV-7 and COMP-5 and COMP-6 were cured on a Fusion DRSE-120 conveyor equipped with Fusion VPS/1600 lamp (D-bulb) at 40 m/min at full power of the lamp. The degree of curing was evaluated using a Q-tip. A sample was considered as fully cured at the moment scratching with a Q-tip caused no visual damage. The results are summarized in Table 8.

TABLE 8

| Radiation curable sample | Degree of curing at 40 m/min |
|---|---|
| INV-5 | Fully cured |
| INV-6 | Fully cured |
| INV-7 | Fully cured |
| COMP-5 | Fully cured |
| COMP-6 | Fully cured |

From Table 8, it becomes apparent that the radiation curable compositions according to preferred embodiments of the present invention are highly sensitive.

Example 4

This example illustrates that the radiation curable inkjet inks according to a preferred embodiment of the present invention exhibit a high curing speed and do not have the undesirable yellowing behaviour of ITX.

Preparation of Radiation Curable Inkjet Inks

The comparative radiation curable compositions COMP-7 and COMP-8 and the inventive radiation curable compositions INV-8 to INV-12 were prepared according to Table 9. The same concentrated pigment dispersions DISP-1 and DISP-2 of EXAMPLE 3 were used. The weight % (wt %) was based on the total weight of the radiation curable compositions.

TABLE 9

| wt % of | INV-8 | INV-9 | INV-10 | INV-11 | INV-12 | COMP-7 | COMP-8 |
|---|---|---|---|---|---|---|---|
| DPGDA | — | 64.6 | — | 66.5 | — | — | 69.0 |
| VEEA | 24.5 | — | 26.5 | — | 24.5 | 30.0 | — |
| TMPTA | 38.6 | — | 38.6 | — | 38.6 | 40.0 | — |
| GENORAD™ 16 | 0.8 | 0.8 | 0.8 | 0.9 | 0.8 | 0.9 | 0.9 |
| EPD | 2.5 | 5.0 | 2.5 | 5.0 | 2.5 | 2.5 | 5.0 |
| ITX | — | — | — | — | — | 2.5 | 5.0 |
| TPO | — | 5.0 | — | 5.0 | — | — | 5.0 |
| IC907 | 4.0 | — | 4.0 | — | 4.0 | 4.0 | — |
| INI-5 | 9.5 | 9.5 | — | — | — | — | — |
| INI-10 | — | — | 7.5 | 7.5 | — | — | — |
| INI-8 | — | — | — | — | 9.5 | — | — |
| DISP-1 | 20.0 | — | 20.0 | — | 20.0 | 20.0 | — |
| DISP-2 | — | 15.0 | — | 15.0 | — | — | 15.0 |
| BYK™ UV3510 | 0.1 | 0.1 | 0.1 | 0.1 | 0.1 | 0.1 | 0.1 |

The comparative radiation curable compositions COMP-7 and COMP-8 and inventive radiation curable compositions INV-8 to INV-12 were coated on PGA-paper, using a bar coater and a 10 μm wired bar. The coated samples were mounted on a belt, transporting the samples under a Phoseon 4W 395 nm LED at a speed of 5 m/min and 10 m/min respectively. The degree of conversion was determined and the results are summarized in Table 10.

TABLE 10

| Radiation curable sample | Degree of conversion at 5 m/min | Degree of conversion at 10 m/min |
| --- | --- | --- |
| INV-8 | 84 | 78 |
| INV-9 | 94 | 88 |
| INV-10 | 79 | 72 |
| INV-11 | 87 | 80 |
| INV-12 | 83 | 76 |
| COMP-7 | 85 | 76 |
| COMP-8 | 94 | 89 |

From Table 10, it becomes clear that the initiators according to preferred embodiments of the present invention result in a comparable degree of conversion compared to thioxanthone based compositions with a comparable composition (INV-8, INV-10, INV-12 and COMP-7; INV-9, INV-11 and COMP-8).

High contents of thioxanthone in radiation curable compositions are known to give high sensitivity for LED curing but result in an instable yellowing behaviour. Therefore, the comparative radiation curable composition COMP-8, having a high ITX content, and the corresponding inventive radiation curable compositions INV-9 and INV-11 were studied more in depth for their yellowing behaviour.

The radiation curable compositions INV-9 and INV-11 and COMP-8 were cured with a Phoseon 4W 395 nm LED, passing the sample 4 times under the LED at a speed of 5 m/min. The stability of the image tone was quantified by measuring the shift in b-value between the freshly printed sample and the sample stored for 7 days at ambient temperature. The results are summarized in Table 11.

TABLE 11

| Radiation Curable Sample | Δb |
| --- | --- |
| INV-11 | −3.64 |
| INV-13 | −3.17 |
| COMP-8 | −8.02 |

From Table 11, it becomes apparent that the photoinitiators according to preferred embodiments of the present invention have a significant more stable yellowing behaviour compared to thioxanthones.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

The invention claimed is:

1. A photoinitiator according to Formula (I):

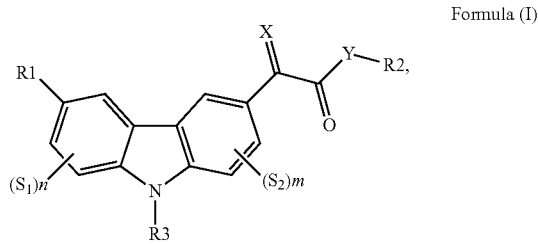

Formula (I)

wherein,

R1 is selected from the group consisting of S1, —CN, —COR4, and a functional group according to Formula (II):

Formula (II)

R2 and R5 are independently selected from the group consisting of hydrogen, an alkyl group, an alkenyl group, an alkynyl group, an aralkyl group, an alkaryl group, and an aryl or heteroaryl group;

S1 and S2 are independently selected from the group consisting of hydrogen, an alkyl group, an alkenyl group, an alkynyl group, an aralkyl group, an alkaryl group, an aryl or heteroaryl group, a halogen, —OH group, an alkoxy group, a thiol group, a thioalkoxy group, an ester group, an amide group, an amine group, and a carboxylic acid group;

R3 is selected from the group consisting of hydrogen, an alkyl group, an alkenyl group, an alkynyl group, an aralkyl group, an alkaryl group, and an aryl or heteroaryl group;

R4 is selected from the group consisting of hydrogen, an alkyl group, an alkenyl group, an alkynynl group, an aralkyl group, an alkaryl group, an aryl or heteroaryl group, and W—R6;

Q and X independently represent O or N—R7;

W, V, and Y independently represent O or N—R8;

R6 and R8 independently are selected from the group consisting of hydrogen, an alkyl group, an alkenyl group, an alkynyl group, an aralkyl group, an alkaryl group, and an aryl or heteroaryl group;

R7 is selected from the group consisting of hydrogen, an alkyl group, an alkenyl group, an alkynyl group, an aralkyl group, an alkaryl group, an aryl or heteroaryl group, and O—R9;

R9 is selected from the group consisting of hydrogen, an alkyl group, an alkenyl group, an alkynyl group, an aralkyl group, an alkaryl group, an aryl or heteroaryl group, and an acyl group;

n and m represent independently an integer from 1 to 3;

with the proviso that at least one of R1 to R3 comprises a branched, substituted or unsubstituted alkyl, alkenyl, alkynyl, aralkyl, or alkaryl group; and substituted means that a substituent is present containing at least one atom different from carbon or hydrogen.

2. The photoinitiator according to claim 1, wherein R1 is selected from the group consisting of hydrogen, —COR4, and a functional group according to Formula (II).

3. The photoinitiator according to claim 1, wherein Q and X represent O.

4. The photoinitiator according to claim 2, wherein Q and X represent O.

5. The photoinitiator according to claim 1, wherein $S_1$ and $S_2$ represent hydrogen.

6. The photoinitiator according to claim 2, wherein $S_1$ and $S_2$ represent hydrogen.

7. The photoinitiator according to claim 3, wherein $S_1$ and $S_2$ represent hydrogen.

8. The photoinitiator according to claim 1, wherein R3 represents a branched alkyl group.

9. The photoinitiator according to claim 2, wherein R3 represents a branched alkyl group.

10. The photoinitiator according to claim 3, wherein R3 represents a branched alkyl group.

11. The photoinitiator according to claim 4, wherein R3 represents a branched alkyl group.

12. The photoinitiator according to claim 1, wherein the photoinitiator is a diffusion hindered photoinitiator selected from the group consisting of a polymerizable photoinitiator, a multifunctional photoinitiator, and a polymeric or an oligomeric photoinitiator.

13. The photoinitiator according to claim 12, wherein the photoinitiator further comprises at least one polymerizable ethylenically unsaturated group selected from the group consisting of an acrylate, a methacrylate, an acrylamide, a methacrylamide, a styrene, a maleimide, a vinyl ester, a vinyl ether, an allyl ether, and an allyl ester.

14. The photoinitiator according to claim 13, wherein at least one of R1 to R3 is substituted with the at least one polymerizable ethylenically unsaturated group.

15. The photoinitiator according to claim 12, wherein one of the groups selected from R1 to R3, $S_1$, and $S_2$ is linked to a polymer selected from the group consisting of a star polymer, a dendritic polymer, and a hyperbranched polymer.

16. The photoinitiator according to claim 15, wherein the hyperbranched polymer is a polyether or a polyester.

17. The photoinitiator according to claim 1, wherein the photoinitiator has a chemical structure according to Formula (III):

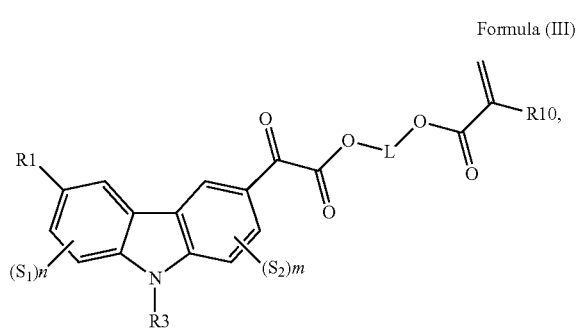

Formula (III)

wherein,
R1, R3, $S_1$, $S_2$, n, and m are the same in as Formula (I);
L is a divalent linking group comprising 1 to 15 carbon atoms; and
R10 represents hydrogen or a C1 to C4 alkyl group.

18. The photoinitiator according to claim 17, wherein R10 represents hydrogen or a methyl group.

19. A radiation curable composition comprising:
a photoinitiator as defined by claim 1.

20. A method for preparing a radiation curable composition as defined by claim 19 comprising the steps of:
a) providing a composition containing monomers; and
b) adding to the composition at least one photoinitiator according to Formula (I) and at least one co-initiator selected from the group consisting of an aliphatic tertiary amine and a dialkyl aniline derivative.

* * * * *